US008187877B2

(12) United States Patent
Bowdish et al.

(10) Patent No.: US 8,187,877 B2
(45) Date of Patent: *May 29, 2012

(54) CHRONIC LYMPHOCYTIC LEUKEMIA CELL LINE

(75) Inventors: Katherine S. Bowdish, Del Mar, CA (US); John McWhirter, San Diego, CA (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 19 days.

This patent is subject to a terminal disclaimer.

(21) Appl. No.: 12/286,759

(22) Filed: Sep. 30, 2008

(65) Prior Publication Data

US 2011/0129471 A1    Jun. 2, 2011

Related U.S. Application Data

(63) Continuation of application No. 10/379,151, filed on Mar. 4, 2003, now Pat. No. 7,435,412, which is a continuation-in-part of application No. PCT/US01/47931, filed on Dec. 10, 2001.

(60) Provisional application No. 60/254,113, filed on Dec. 8, 2000.

(51) Int. Cl.
*C12N 5/09* (2010.01)
*C12N 5/0781* (2010.01)

(52) U.S. Cl. ..................... 435/372; 435/372.2

(58) Field of Classification Search .......... None
See application file for complete search history.

(56) References Cited

U.S. PATENT DOCUMENTS

| | | | |
|---|---|---|---|
| 3,940,475 A | 2/1976 | Gross | |
| 4,289,747 A | 9/1981 | Chu | |
| 4,376,110 A | 3/1983 | David et al. | |
| 5,223,409 A | 6/1993 | Ladner et al. | |
| 5,225,539 A * | 7/1993 | Winter | 530/387.3 |
| 5,403,484 A | 4/1995 | Ladner et al. | |
| 5,427,908 A | 6/1995 | Dower et al. | |
| 5,434,131 A | 7/1995 | Linsley et al. | |
| 5,508,717 A | 4/1996 | Miller | |
| 5,571,698 A | 11/1996 | Ladner et al. | |
| 5,580,717 A | 12/1996 | Dower et al. | |
| 5,780,279 A | 7/1998 | Matthews et al. | |
| 5,859,205 A | 1/1999 | Adair et al. | |
| 5,902,583 A | 5/1999 | Buchsbaum et al. | |
| 5,916,560 A | 6/1999 | Larsen et al. | |
| 6,011,138 A | 1/2000 | Reff et al. | |
| 6,040,136 A | 3/2000 | Garrard et al. | |
| 6,338,851 B1 | 1/2002 | Gorczynski | |
| 6,632,927 B2 | 10/2003 | Adair et al. | |
| 6,652,858 B2 | 11/2003 | Gorczynski et al. | |
| 6,737,056 B1 | 5/2004 | Presta | |
| 6,749,854 B2 | 6/2004 | Gorczynski et al. | |
| 6,955,811 B2 | 10/2005 | Gorczynski et al. | |
| 6,984,625 B2 | 1/2006 | Gorczynski | |
| 7,238,352 B2 | 7/2007 | Gorczynski et al. | |
| 2002/0031515 A1 | 3/2002 | Caligiuri et al. | |
| 2002/0168364 A1 | 11/2002 | Gorczynski et al. | |
| 2002/0192215 A1 | 12/2002 | Hoek et al. | |
| 2003/0017491 A1 | 1/2003 | Shi et al. | |
| 2004/0018972 A1 | 1/2004 | Gorczynski et al. | |
| 2004/0054145 A1 | 3/2004 | Gorczynski | |
| 2004/0175692 A1 | 9/2004 | Bowdish et al. | |
| 2004/0198661 A1 | 10/2004 | Bowdish et al. | |
| 2005/0048069 A1 | 3/2005 | Gorczynski et al. | |
| 2005/0107314 A1 | 5/2005 | Gorczynski et al. | |
| 2005/0129690 A1 | 6/2005 | Bowdish et al. | |
| 2005/0169870 A1 | 8/2005 | Truitt et al. | |
| 2006/0024231 A1 | 2/2006 | Schnitzer et al. | |
| 2007/0065438 A1 | 3/2007 | Liversidge et al. | |
| 2008/0131428 A1 | 6/2008 | Young et al. | |

FOREIGN PATENT DOCUMENTS

| | | |
|---|---|---|
| JP | 02-046297 | 2/1990 |
| WO | WO-8403508 A1 | 9/1984 |
| WO | WO-8503508 A1 | 8/1985 |
| WO | WO-9215679 A1 | 9/1992 |
| WO | WO-9428027 | 12/1994 |
| WO | WO-9518825 | 7/1995 |
| WO | WO-9627011 A1 | 9/1996 |
| WO | WO-9638557 | 12/1996 |
| WO | WO-9708320 A1 | 3/1997 |
| WO | WO-9721450 A | 6/1997 |
| WO | WO-8806630 A1 | 9/1998 |
| WO | WO-9924565 | 5/1999 |
| WO | WO-01/87336 A1 | 11/2001 |
| WO | WO-0211762 A2 | 2/2002 |
| WO | WO-0242332 A2 | 5/2002 |
| WO | WO-02/059280 | 8/2002 |
| WO | WO-02095030 | 11/2002 |
| WO | WO-03025202 A2 | 3/2003 |
| WO | WO 2004/060295 A2 | 7/2004 |
| WO | WO-2004078937 A2 | 9/2004 |
| WO | WO-2004078938 | 9/2004 |

(Continued)

OTHER PUBLICATIONS

Clark (Protein Engineering of Antibody Molecules for Prophylactic and Therapeutic Applications in Man, 1993, pp. 4-5).*
Simelyte et al., "CD200-Fc, a Novel Antiarthritic Biologic Agent That Targets Proinflammatory Cytokine Expression in the Joints of Mice With Collagen-Induced Arthritis," Arthritis & Rheumatism, vol. 58(4), pp. 1038-1043 (2008).
Alizadeh et al., "Distinct types of diffuse large B-cell lymphoma identified by gene expression profiling," Nature, 403:503-511(2000).
Auchincloss et al. "Strategies to Induce Tolerance," Transplantation Immunology, Bach and Auchincloss, Eds., Wiley-Liss, New York, Chapter 11, pp. 211-218 (1995).
Bach, "Immunosuppressive therapy of autoimmune diseases," Immunology Today, 14(6)322-326(1993).
Banerjee, D., et al., "Blocking CD200-CD200 receptor axis augments NOS-2 expression and aggravates experimental autoimmune uveoretinitis in Lewis rats," Ocular Immunology and Inflammation, 12(2):115-125 (2004).

(Continued)

*Primary Examiner* — Karen Canella
(74) *Attorney, Agent, or Firm* — Ropes & Gray LLP

(57) ABSTRACT

The preparation and characterization of antibodies that bind to antigens on CLL or other cancer cells, especially to antigens upregulated in the cancer cells, and the identification and characterization of antigens present on or upregulated by cancer cells are useful in studying and treating cancer.

1 Claim, 23 Drawing Sheets

FOREIGN PATENT DOCUMENTS

| WO | WO 2005/007809 A2 | 1/2005 |
|----|-------------------|--------|
| WO | WO 2006/053301 A2 | 5/2006 |
| WO | WO 2007/084321 A2 | 7/2007 |

OTHER PUBLICATIONS

Barclay and Ward, "Purification and Chemical Characterisation of Membrane Glycoproteins From Rat Thymocytes and Brain, Recognised by Monoclonal Antibody MRC OX2," European J. Biochemistry, 129:447-458(1982).

Barclay et al.,"CD200 and membrane protein interactions in the control of myeloid cells," Trends in Immunology, 23(6):2002.

Barclay, A.N., "Different reticular elements in rat lymphoid tissue identified by localization of Ia, Thy-1 and MRC OX 2 antigens," Immunology, 44:727-736 (1981).

Barclay, A.N., et al., "Neuronal/Lymphoid Membrane Glycoprotein MRC OX-2 is a Member of the Immunoglobulin Superfamily with a Light-Chain-Like Structure," Biochem. Soc. Symp., 51:149-157 (1985).

Bauvois et al., Constitutive expression of CD26/dipeptidylpepidase IV on peripheral blood B lymphocytes of patients with B chronic lymphocytic leukaemia. British Journal of Cancer 1999., vol. 79. p. 1042-1048.

Blazer, B.R., et al., "CD28/B7 Interactions Are Required for Sustaining the Graft-Versus-Leukemia Effect of Delayed Post-Bone Marrow Transplantation Splenocyte Infusion in Murine Recipients of Myeloid or Lymphoid Leukemia Cells," J. Immunol., 159:3460-3473 (1997).

Bohen, S.P., "Variation in gene expression patterns in follicular lymphoma and the response to rituximab," PNAS, 100(4):1926-1930(2003).

Boon, Thierry., "Toward a Genetic Analysis of Tumor Rejection Antigens," Advances in Cancer Res., 58:177-210(1992).

Borriello et al., "MRC OX-2 Defines a Novel T Cell Costimulatory Pathway," J. Immunol., 158:4549-4554(1997).

Borriello, F., et al., "Characterization and localization of Mox2, the gene encoding the murine homolog of the rat MRC OX-2 membrane glycoprotein," Mammalian Genome, 9(2):114-118 (1998).

Broderick et al., "Constitutive Retinal CD200 Expression Regulates Resident Microglia and Activin State of Inflammatory Cells During Experimental Autoimmune Uveoretinitis," Am. J. of Pathology, 161(5):1669-1677(2002).

Brody et al. "Human Cancer Detection and Immunotherapy with Conjugated and Non-Conjugated Monoclonal Antibodies" Anticancer Research 16: 661-674 (1996).

Bukovsky, A., et al., "Association of lymphoid cell markers with rat ascitic malignant cells," IRCS Med. Sci., 11:866-867 (1983).

Bukovsky, A., et al., "Association of some cell surface antigens of lymphoid cells and cell surface differentiation antigens with early rat pregnancy," Immunology, 52:631-640 (1984).

Bukovsky, A., et al., "The localization of Thy-1.1, MRC OX 2 and Ia antigens in the rat ovary and follopian tube," Immunology, 48:587-596 (1983).

Bukovsky, A., et al., "The ovarian follicle as a model for the cell-mediated control of tissue growth," Cell Tissue Res., 236:717-724 (1984).

Caldas et al., "Humanization of the anti-CD18 antibody 6.7: an unexpected effect of a framework residue in binding to antigen," Mol. Immunol. 39:941-952 (2003).

Chaouat and Clark, FAS/FAS Ligand Interaction at the Placental Interface is not Required for the Success of Allogeneic Pregnancy in Anti-Paternal MHC Preimmunized Mice, Presented at the 6th Congress of the Adria-Alps Soc. of Immunol. of Reprod., (2000) / Amer. J. of Reprod. Immunol., 45:108-115(2001).

Chen, D., et al., "Discrete Monoclonal Antibodies Define Functionally Important Epitopes in the CD200 Molecule Responsible for Immunosupression Function," Transplantation, 79:282-288 (2005).

Chen, D., et al., "Synthetic peptides from the N-terminal regionsl of CD200 and CD200R1 modulate immunosupressive and anti-inflammatory effects of CD200-CD200R1 interaction," International Immunology, 17(3):289-296 (2005).

Chen, Z., et al., "Cloning and characterization of the murine homologue of the rat/human MRC OX-2 gene," Database Medline, Biochemica et Biophysica Acta, 1362(1):6-10 (1997).

Cherwinski, H.M., et al., "The CD200 Receptor Is a Novel and Potent Regulator of Murine and Human Mast Cell Function," J. Immunol., 174:1348-1356 (2005).

Chien et al., "Significant structural and functional change of an antigen-binding site by a distant amino acid substitution: proposal of a structural mechanism," Proc. Natl. Acad. Sci. USA 86:5532-5536 (1989).

Chitnis et al., "The Role of CD200 in Immune-Modulation and Neural Protection in EAE," Abstract, 12th International Congress of Immunology and 4th Annual Conference of FOCIS, Montreal, Jul. 21, 2004.

Chitnis, T., et al., "Elevated Neuronal Expression of CD200 Protects $Wld^s$ Mice from Inflammation-Mediated Neurodegeneration," American Journal of Pathology, 170(5):1695-1712 (2007).

Clark et al., "Fgl2 prothrombinase expression in mouse trophoblast and decidua triggers abortion but may be countered by OX-2," Mol. Human Reprod., 7:185-194(2001).

Clark et al., "Labile CD200 tolerance signal important in transfusion-related immunomodulation (TRIM) prevention of recurrent miscarriages," Amer. J. Reprod. Immunol., 45:361(2001).

Clark et al., "Procoagulants in fetus rejection: the role of the OX-2 (CD200) tolerance signal," Seminars in Immunol., 13(4)255-263(2001).

Clark et al., "The OX-2 Tolerance Signal Molecule at the Fetomaternal Interface Determines Pregnancy Outcome," Amer. Journal of Reprod Immunol., 43:326(2000). Abstract Only.

Clark et al., Amer. Soc. for Reprod. Medicine, 55th Annual Meeting (1999).

Clark, D.A., "Intralipid as Treatment for Recurrent Unexplained Abortion?", Am. J. of Reprod. Immunol., 32:290-293(1994).

Clark, M.J., et al., "MRC OX-2 antigen: a lymphoid/neuronal membrane glycoprotein with a structure like a single immunoglobulin light chain," EMBO Journal, 4(1):113-118 (1985).

Clarke, M.J., "MRC OX-2 lymphoid brain glycoprotein: S1 mapping suggests higher levels of abnormal RNA in the thymus than in the brain," Biochemical Society Transactions, 14:80-81 (1986).

Cochlovius et al., "Cure of Burkitt's Lymphome in Severe Combined Immunodeficiency Mice by T Cells, Tetravalent CD3×CD19 Tandem Diabody, and CD28 Costimulation," Cancer Res. 60:4336-4341 (2000).

Cohen, P.L., "Systemic Autoimmunity," in Fundamental Immunology, Fourth edition, W.E. Paul, Editor, Lippincott-Raven Publishers, Philadelphia, Ch. 33, p. 1067-1088(1999).

Database Medline, abstract No. NLM16160950, Rioux P. 1999.

DeNardo et al., "Increased Survival Associated with Radiolabeled Lym-1 Therapy for Non-Hodgkin's Lymphoma and Chronic Lymphocytic Leukemia." Cancer Supplement (1997) vol. 80, No. 12. pp. 2706-2711.

Dennis, C., "Off by a whisker," Nature, 442,:739-741 (2006).

Dick et al., "Control of Myeloid Activity During Retinal Inflammation," J. of Leukocyte Bio., 74:161-166(2003).

Ebert et al., "Selective Immunosuppressive Action of a Factor Produced by Colon Cancer Cells," Cancer Res. 50:6158-6161 (1990).

Elgert, K. D. "Immunology : Understanding the Immune System," The Genetic Basis of Antibody Diversity, 123 (1996).

Faguet et al., "Blood Kinectics, Tissue Distribution, and Radioimaging of Anti-Common Chronic Lymphatic Leukemia Antigen (cCLLa) Monoclonal Antibody $CLL_2$ in Mice Transplanted With cCLLa-Bearing Human Leukemia Cells." Blood. vol. 75, No. 9 (1990) pp. 1853-1861.

Faisal et al., Cell-surface Associated p43/Endothelial-monocyte-activating-polypeptide-II in Hepatocellular Carcinoma Cells Induces Apoptosis in T-lynphocytes, Asian J. of Surg. 30(1):13-22 (2007).

Fallarino, F., et al., "Murine Plasmacytoid Dendritic Cells Initiate the Immunosupressive Pathway of Tryptophan Catabolism in Response to CD200 Receptor Engagement," J. Immunol., 173:3748-3754 (2004).

Farber, U., et al., "Loss of heterozygosity on chromosome 3, bands q24->qter, in a diploid meningioma," Cytogenet Cell Genet, 57:157-158 (1991).

Feuerstein et al., 1999, Induction of Autoimmunity in a Transgenic Model of B Cell Receptor Peripheral Tolerance: Changes in Coreceptors and B Cell Receptor-Induced Tyrosine-Phosphoproteins, J. Immunol. 163:5287-5297.

Funakoshi et al., "Antitumor Effects of Nonconjugated Murine Lym-2 and Human-Mouse Chimeric CLL-1 Monoclonal Antibodies Against Various Human Lumphoma Cell Lines In Vitro and In Vivo." Blood vol. 90, No. 8 (1997) pp. 3150-3166.

Ginaldi et al., "Levels of expression of CD52 in normal and leukemic B and T cells: correlation with in vivo therapeutic responses to Campath-1H," Leukemia Res. 22(2):185-191 (1998).

Giusti et al., "Somatic diversification of S107 from an antiphosphocholine to an anti-DNA autoantibody is due to a single base change in its heavy chain variable region," Proc. Natl. Acad. Sci. USA 84:2926-2930 (1987).

Gorczynski and Marsden, "Modulation of CD200 receptors as a novel method of immunosuppression," Expert Opin. Ther. Patents, 13(5): 711-715(2003). See also WIPO Patent No. WO02095030 assigned to Transplantation Tech, Inc.

Gorczynski et al., "Anti-CD200R Ameliorates Collagen-Induced Arthritis in Mice," J. of Immunol., 104(3):256-264(2002).

Gorczynski et al., "Does Successful Allopregnancy Mimic Transplantation Tolerance?", Graft, 4:338-345(2001).

Gorczynski et al., "Evidence of a role for CD200 in regulation of immune rejection of leukaemic tumour cells in C57BL/6 mice," Clin. Exp. Immunol., 126:220-229(2001).

Gorczynski et al., Transplantation, 65(8):1106-1114(1998).

Gorczynski, "CD200 and Its Receptors as Targets for Imnnnoregulation" Current Opinion in Investigational Drugs, Pharmapress, US, vol. 6, No. 5, May 2005, pp. 483-488. XP008051169 ISSN: 1472-4472.

Gorczynski, Current Opinion in Investigational Drugs, 6:483-488(2005).

Gorczynski, L., et al., "Evidence That an OX-2-Positive Cell Can Inhibit the Stimulation of Type 1 Cytokine Production by Bone Marrow-Derived B7-1 (and B7-2)-Positive Dendtritic Cells," J. Immunol., 162:774-781 (1999).

Gorczynski, R., et al., "CD200 Is a Ligand for All Members of the CD200R Family of Immunoregulatory Molecules," J. Immunol., 172:7744-7749 (2004).

Gorczynski, R., et al., "Dendritic Cells Expressing TGFBeta/IL-10, and CHO Cells With OX-2, Increase Graft Survival," Transplantation Proceedings, 33:1565-1566 (2001).

Gorczynski, R.M., "Evidence for an Immunoregulatory Role of OX2 with Its Counter Ligan (OX2L) in the Regulation of Transplant Rejection, Fetal Loss, Autoimmunity and Tumor Growth", Arch Immunol. Ther Exp (Warsz), PMID 11726033 (Pubmed Indexed for Medline), 49(4):303-309 (2001).

Gorczynski, R.M., "Role of Cytokines in Allograft Rejection," Current Pharmaceutical Design, 7:1039-1057 (2001).

Gorczynski, R.M., "Synergy in Induction of Increased Renal Allograft Survival after Portal Vein Infusion of Dendtritic Cells Transduced to Express TGFB and IL-10, along with Administration of CHO Cells Expressing the Regulatory Molecule OX-2," Clinical Immunology, 95(3):182-189 (2000).

Gorczynski, R.M., "Transplant tolerance modifying antibody to CD200 receptor, but not CD200, alters cytokine production profile from stimulated macrophages," Eur. J. Immunol., 31:2331-2337 (2001).

Gorczynski, R.M., et al., "A CD200FC Immunoadhesin Prolongs Rat Islet Xenograft Survival in Mice," Transplantation, 73(12):1948-1953 (2002).

Gorczynski, R.M., et al., "An Immunoadhesin Incorporating the Molecule OX-2 is a Potent Immunosuppressant That Prolongs Allo- and Xenograft Survival," J. Immunol., 163:1654-1660(1999).

Gorczynski, R.M., et al., "Anti-Rat OX-2 Blocks Increased Small Intestinal Transplant Survival After Portal Vein Immunization," Transplantation Proceedings, 31:577-578 (1999).

Gorczynski, R.M., et al., "Augmented Induction of CD4+ CD25+ Treg using Monoclonal Antibodies to CD200R," Transplantation, 79(4):488-491 (2005).

Gorczynski, R.M., et al., "Augmented Induction of CD4+ CD25+ Treg using Monoclonal Antibodies to CD200R," Transplantation, 79(9):1180-1183 (2005).

Gorczynski, R.M., et al., "CD200 Immunoadhesin Supresses Collagen-Induced Arthritis in Mice," Clinical Immunology, 101(3):328-334 (2001).

Gorczynski, R.M., et al., "Evidence for Persistent Expression of OX2 as a Necessary Component of Prolonged Renal Allograft Survival Following Portal Vein Immunization," Clinical Immunol., 97(1):69-78 (2000).

Gorczynski, R.M., et al., "Increased Expression of the Novel Molecule OX-2 is Involved in Prolongation of Murine Renal Allograft Survival," Transplantation, 65(8):1106-1114 (1998).

Gorczynski, R.M., et al., "Induction of Tolerance-Inducing Antigen-Presenting Cells in Bone Marrow Cultures in Vitor Using Monoclonal Antibodies to CD200R," Transplantation, 77(8):1138-1144 (2004).

Gorczynski, R.M., et al., "Interleukin-13, in Combination with Anti-Interleukin-12, Increases Graft Prolongation After Portal Venous Immunization with Cultured Allogeneic Bone Marrow-Derived Dentritic Cells," Transplantation, 62(11):1592-1600 (1996).

Gorczynski, R.M., et al., "Persistent expression of OX-2 is necessary for renal allograft survival," FASEB Journal, 14(6):A1069 (2000).

Gorczynski, R.M., et al., "Receptor Engagement on Cells Expressing a Ligand for the Tolerance-Inducing Molecule OX2 Induces an Immunoregulatory Population That Inhibits Alloreactivity In Vitro and In Vivo," J. Immunol., 165:4854-4860 (2000).

Gorczynski, R.M., et al., "Regulation of Gene Expression of Murine MD-1 Regulates Subsequent T Cell Activation and Cytokine Production," J. of Immunology, 165:1925-1932 (2000).

Gorczynski, R.M., et al., "Structural and Functional Heterogeneity in the CD200R Family of Immunoregulatory Molecules and their Expression at the Fetomaternal Interface," AJRI, 52:147-163 (2004).

Gorczynski, R.M., et al., "The Same Immunoregulatory Molecules Contribute to Successful Pregnancy and Transplantation," AJRI, 48:18-26 (2002).

Gorczynski,"Evidence for an Immunoregulartory Role of OX2 with its Counter Ligand (OX2L) in the Regulation of Transplant Rejection, Fetal Loss, Autoimmunity and Tumor Growth," Archibum Immunologiae et Therapiae Experimentalis, vol. 49(4) pp. 303-309 (2001).

Gura, T., "Systems for Identifying New Drugs Are Often Faulty," Science, 278:1041-1042 (1997).

Gussow and Seemann, "Humanization of Monoclonal Antibodies," Meth. Enzymol. 203:99-121 (1991).

Hardy et al., "A lymphocyte-activating monoclonal antibody induces regression of human tumors in severe combined immunodeficient mice," Proc. Natl. Acad. Sci. USA 94:5756-5760 (1997).

Hart, P.H., "Modulation of Monocyte Effector Functions by Lipopolysacc-haride and Interferon-Y," Dept. of Medicine, University of Melbourne, Royal Melbourne Hospital, Parkville, Vic., 3050 (Abstract).

Heaney et al., "Severe asthma treatment: need for characterising patients," Lancet, 365:974-976(2005).

Hoek, R.M., et al., "Down-Regulation of the Macrophage Lineage Through Interaction with OX2 (CD200)," Science, 290:1768-1771 (2000).

Hoek, R.M., et al., "Macrophage regulation by the B7.1/2 homologue OX2?", FASB Journal, 14(6):A1232 (2000).

Huang, "Structural chemistry and therapeutic intervention of protein-protein interactions in immune response, human immunodeficiency virus entry, and apoptosis," Pharmacol. Therapeutics, 86:201-215(2000).

Hutchings, N.J., et al., "Interactions of Cytoplasmic Region of OX2R Are Consistent with an Inhibitory Function," Annual Congress of the British Society for Immunology, Dec. 5-8, 2000, Harrogate, UK.

Iwanuma et al., "Antitumor Immune Response of Human Peripheral Blood Lymphocytes Coengrafted with Tumor into Severe Combined Immunodeficient Mice," Cancer Res. 57:2937-2942 (1997).

Jain, "The next frontier of molecular medicine: Delivery of therapeutics," Nature Medicine, 4(6):655-657(1998).

Jansky, L., et al., "Dynamics of Cytokine Production in Human Peripheral Blood Mononuclear Cells Stimulated by LPS or Infected by Borrelia," Physiol. Res., 52:593-598 (2003).

Jeurissen, S.H.M., et al., "Characteristics and functional aspects of nonlymphoid cells in rat germinal centers, recognized by two monoclonal antibodies ED5 and ED6," Eur. J. Immunol., 16:562-568 (1986).

Keil et al., Amer. J. Reprod. Immunol., 45:343(2001).

Kim et al., "Divergent Effects of 4-1BB Antibodies on Antitumor Immunity and on Tumor-reactive T-Cell Generation," Cancer Res., 61:2031-2037(2001).

Kjaergaard et al., "Therapeutic Efficacy of OX-40 Receptor antibody Depends on Tumor Immunogenicity and Anatomic Site of Tumor Growth," Cancer Res. 60:5514-5521(2000).

Kneitz, C., et al., "Inhibition of Tcell/B cell interaction by B-CLL cells," Leukemia, 13:98-104 (1999).

Kretz-Rommel, "CD200 Expression on Tumor Cells Suppresses Antitumor Immunity: New Approaches to Cancer Immunotherapy," J. Immunol. 178:5595-5605 (2007).

Kretz-Rommel, A., et al., "CD200 Expression on Tumor Cells Suppresses Anti-Tumor Immunity: New Approaches to Cancer Immunotherapy," J. Immunother., 29(6):666 (2006).

Kretz-Rommel, A., et al., "Immune Evasion by CD200: New Approaches to Targeted Therapies for Chronic Lymphocytic Leukemia," J. Immunother., 28(6):650 (2005).

Kretz-Rommel, A., et al., "The Immuno-Regulatory Protein CD200 Is Overexpressed in a Subset of B-Cell Chronic Lymphocytic Leukemias and Plays a Role in Down-Regulating the TH1 Immune Response," J. Immunother., 27(6):546 (2004).

Kroese, F.G.M., et al., "Germinal centre formation and follicular antigen trapping in the spleen of lethally X-irradiated and reconstituted rats," Immunology, 57:99-104 (1986).

Kroese, F.G.M., et al., "The ontogeny of germinal centre forming capacity of neonatal rat spleen," Immunology, 60:597-602 (1987).

Liu et al., "Effect of combined T- and B-cell depletion of allogenic HLA-mismatched bone marrow graft on the magnitude and kinetics of Epstein-Barr virus load in the peripheral blood of bone marrow transplant recipients," Clin. Transplant. 18:518-524 (2004).

Mariuzza et al., "The Structural Basis of Antigen-Antibody Recognition," Ann. Rev. Biophys. Biophys. Chem. 16:139-159 (1987).

Marsh, M.N., "Functional and Structural Aspects of the Epithelial Lymphocyte, with Implications for Coeliac Disease and Tropical Sprue," Univ. Dept. of Medicine, University of Manchester School of Medicine at Hope Hospital, Salford, Manchester UK pp. 55-75 (1985).

Matutes et al. Morphological and Immuniphenotypic Features of Chronic Lymphocytic Leukemia. Rev. Clin. Exp. Hematol. vol. 4.1, Mar. 2000 p. 22-47.

McCaughan et al., "Characterization of the Human Homolog of the Rat MRC OX-2 Membrane Glycoprotein," Immunogenetics, 25:329-335(1987).

McCaughan, G.M., et al., "Identification of the human homologue of the rat lymphoid/brain antigen MRC OX-2," Australian and New Zealand Journal of Medicine 17: 142 (Abstract) (1987).

McCaughan, G.W., et al., "The Gene for MRC OX-2 Membrane Glycoprotein Is Localized on Human Chromosome 3," Immunogenetics, 25:133-135 (1987).

McMaster, W.R., et al., "Identification of Ia glycoproteins in rat thymus and purification from rat spleen," Eur. J. Immunol., 9:426-433 (1979).

McWhirter, J.R., et al., "Antibodies selected from combinatorial libraries block a tumor antigen that plays a key role in immunomodulation," PNAS, 103(4):1041-1046 (2006).

Mjaaland et al., "Modulation of immune responses with monoclonal antibodies. I. Effects on regional lymph node morphology and on anti-hapten responses to haptenized monoclonal antibodies", Eur. J. Immunol., 20:1457-1461(1990).

Mjaaland, S., et al., "The Localization of Antigen in Lymph Node Follicles of Congenitally Athymic Nude Rats," Scand. J. Immunol., 26:141-147 (1987).

Mohammad, R.M., et al., "Establishment of a human B-CLL xenograft model: utility as a preclinical therapeutic model," Leukemia, 10:130-137 (1996).

Mori et al., "Establishment of a new anit-cancer drugs-resistant cell line derived from B-chronic lymphocyctic leukemia" Proceedings, Fifty-Ninth Annual Meeting of teh Japanese Cancer Association, p. 583, # 3788 (Sep. 1, 2000).

Morris, R.J., et al., "Sequential Expression of OX2 and Thy-1 Glycoproteins on the Neuronal Surface during Development," Dev. Neurosci., 9:33-44 (1987).

Myers et al., "Characterization of a Peptide Analog of a Determinant of Type II Collagen that Suppresses Collagen-Induced Arthritis," J. of Immunology, 3589-3595(1998).

Nagelkerken L., et al., "Accessory Cell Function of Thoracic Duct Nonlymphoid Cells, Dentritic Cells, and Splenic Adherent Cells in the Brown-Norway Rat," Cellular Immunology, 93:520-531 (1985).

Nathan and Muller, "Putting the Brakes on innate immunity: a regulatory role for CD200?", Nat Immunol., 2(1):17-19(2001).

Ni et al., "An immunoadhesin incorporating the molecule OX-2 is a potent immunosuppressant which prolongs allograft survival", FASEB Journal 13(5):A983(1999).

Pardoll, Drew., "Therapeutic Vaccination for Cancer," Clin. Immunol., 95(1):S44-S62(2000).

Paterson, D.J., et al., "Antigens of Activated Rat T Lymphocytes Including A Molecule of 50,000 Mr Detected Only on CD4 Positive T Blasts," Molecular Immunology, 24(12):1281-1290 (1987).

Preston et al., "The leukocyte/neuron cell surface antigen OX2 binds to a ligand on macrophages", European J. of Immunol., 27(8):1911-1918(1997).

Ragheb et al., "Preparation and functional properties of monoclonal antibodies to human, mouse and rat OX-2", Immunol. Letters, 68(2,3):311-315(1999).

Ragheb, R.F., "Exploration of OX-2 function in tolerance induction and graft acceptance using an anti-mouse OX-2 monoclonal antibody," Masters Abstracts International, 38(4):971-972 (2000).

Richards, S.J., et al., "Reported Sequence Homology Between Alzheimer Amyloid770 and the MCR OX-2 Antigen Does Not Predict Function," Brain Research Bulletin, 38(3):305-306 (1995).

Riley, "Melanoma and the Problem of Malignancy," J. Exp. Med. 204:1-9 (2004).

Romagnani, Sergio., "Short Analytical Review: TH1 and TH2 in Human Diseases," Clin. Immunol. Immunopath, 80(3):225-235(1996).

Rosenblum, M.D., et al., "CD200 is a novel p53-target gene involved in apoptosis-associated immune tolerance," Blood, 103(7):2691-2698 (2004).

Rosenwald et al., "Relation of Gene Expression Phenotype to Immunoglobulin Mutation Genotype in B Cell Chronic Lymphocytic Leukemia," J. of Exp. Medicine, 194(11):1639-1647(2001).

Rudicoff et al., "Single amino acid substitution altering antigen-binding specificity," Proc. Natl. Acad. Sci. USA 79:1979-1983 (1982).

Sahin et al., "New monoclonal antibody specific for a 6.5 kDa glycoprotein which presents mainly on a B cell of chronic lymphocytic leukemia (CLL)" Immunology Letters, 2001, 76, 1-6.

Schlom, Jeffrey :Monoclonal Antiboides They're More and Less Than You Think, Molecular and Cellular Research for Future Diagnosis and Therapy, 95-134, 1991.

Schultes et al., "Immunotherapy of Human Ovarian Carcinoma with OVAREX™ MAb-B43.13 in a Human-PBL-SCID/BG Mouse Model," Hybridoma 18(1):47-55 (1999).

Sebestyen et al., Syndecan-1 (CD138) expression in human non-Hodgkin lymphomas. British Jounal of Hematology. vol. 104, 1999, p. 412-419.

Sehgal, et al., "Generation of the Primary Antibody Repertoire in Rabbits: Expression of a Diverse Set of Igk-V Genes May Compensate for Limited Combinatorial Diversity at the Heavy Chain Locus," Immunogenetics 50:31-42 (1999).

Snyder et al., "Enhanced Targeting and Killing of Tumor Cells Expressing the CXC Chemokine Receptor 4 by Transducible Anticancer Peptides," Cancer Res. 65(23):10646-10650 (2005).

Srivastava, P.K., "Immunotherapy of human cancer: lessons from mice," Nature Immunology, 1(5):363-366 (2000).

Steinman, Lawrence., "Assessment of Animal Models for MS and Demyelinating Disease in the Design of Rational Therapy," Neuron, 24:511-514 1999.

Stuart et al., Lab. Invest., 54(1):1-3(1986).
Syme, R., et al., "Comparison of CD34 and Monocyte-Derived Dendritic Cells from Mobilized Peripheral Blood from Cancer Patients," Stem Cells, 23:74-81 (2005).
Tanaka et al., "The Anti-Human Tumor Effect and Generation of Human Cytotoxic T Cells in SCID Mice Given Human Peripheral Blood Lymphocytes by the in Vivo Transfer of the Interleukin-6 Gene Using Adenovirus Vector," Cancer Res. 57:1335-1343 (1997).
Tang et al., Pathogenesis of collagen-induced arthritis: modulation of disease by arthritogenic T-Cell epitope location, J. of Immunology, 113: 384-391.
Tangri and Raghupathy, "Expression of Cytokines in Placentas of Mice Undergoing Immunologically Mediated Spontaneous Fetal Resorptions," Biology of Reprod., 49:850-856(1993).
Taylor, N., et al., "Enhanced Tolerance to Autoimmune Uveitis in CD200-Deficient Mice Correlates with a Pronounced Th2 Switch in Response to Antigen Challenge," J. Immunol., 174:143-154 (2005).
Thomsen et al., "Reconstitution of a human immune system in immunodeficient mice: models of human alloreaction in vivo," Tissue Antigens 66:73-82 (2005).
Toder et al., "Mouse Model for the Treatment of Immune Pregnancy Loss," Am. J. of Reprod. Immunol., 26:42-46(1991).
Webb, M., et al., "Localisation of the MRC OX-2 Glycoprotein on the Surfaces of Neurones," J. Neurochemistry, 43:1061-1067 (1984).
Wilczynski, J.R., "Immunoligical Analogy Between Allograft Rejection, Recurrent Abortion and Pre-Eclampsia—the Same Basic Mechanism?," Human Ummunology, 67:492-511 (2006).
Wright et al., "The unusual distribution of the neuronal/lymphoid cell surface CD200 (OX2) glycoprotein is conserved in himans," Immunology 102:173-179 (2001).
Wright, G.J., et al., "Lymphoid/Neuronal Cell Surface OX2 Glycoprotein Recognizes a Novel Receptor on Macrophages Implicated in the Control of Their Function," Immunity, 13:233-242 (2000).
Wright, G.J., et al., "The lymphoid/neuronal OX-2 glycoprotein interacts with a novel protein expressed by macrophages," Tissue Antigens, 55 (Supplement 1); vol. 11 (2000).
Wright, G.J., et al., "Viral homologues of cell surface proteins OX2 and CD47 have potential to regulate macrophage function," Annual Congress of the British Society for Immunology, vol. 101 (Supplement 1): 50 Dec. 5-8, 2000.
Yang, C., et al., "Functional maturation and recent thymic emigrants in teh periphery: development of alloreactivity correlates with the cyclic expression of CD45RC isoforms," Eur. J. Immunol., 22:2261-2269 (1992).
Yu, X., et al., "The role of B7-CD28 co-stimulation in tumor rejection," International Immunology, 10(6):791-797 (1998).
Zhang, S., et al., "Molecular Mechanisms of CD200 Inhibition of Mast Cell Activation," J. Immunol., 173:6786-6793 (2004).

Zheng, P., et al., "B7-CTLA4 interaction enhances both production of antitumor cytotoxic T lymphocytes and resistance to tumor challenge," Proc. Natl. Acad. Sci. USA, 95:6284-6289 (1998).
Zhu et al., "Radioimmunotherapy of Human B-Cell Chronic Lymphocytic Leukemia in Nude Mice." Cancer Research. 54, 5111-5117.
Zips, D., et al., "New Anticancer Agents: In Vitro and In Vivo Evaluation," in vivo, 19:1-7 (2005).
Zou et al. Human Glioma-Induced Immunosuppression Involves Soluble Factor(s) That Alters Monocyte Cytokine Profile and Surface Markers. Apr. 15, 1999. vol. 162, pp. 4882-4892.
Bruggemann et al., "A Matched Set of Rat/Mouse Chimeric Antibodies: Identification and Biological Properties of Rat H Chain Constant Regions $\mu$, $\gamma 1$, $\gamma 2a$, $\gamma 2b$, $\gamma 2c$, $\epsilon$, and $\alpha^1$," The Journal of Immunology, vol. 142(9), pp. 3145-3150 (1989).
Ohno et al., "Antigen-binding specificities of antibodies are primarily determined by seven residues of $V_H$," Proc. Natl. Acad. Sci., vol. 82, pp. 2945-2949 (1985).
Pakula and Sauer, "Genetic analysis of protein stability and function," Annu. Rev. Genet., vol. 23, pp. 289-310 (1989).
Panka et al., "Variable region framework differences result in decreased or increased affinity of variant anti-digoxin antibodies," Proc, Natl. Acad. Sci. USA, vol. 85:3080-3084 (1988).
Tao et al., "Structural Features of Human Immunoglobulin G that Determine Isotype-specific Differences in Complement Activation," J. Exp. Med., vol. 178, pp. 661-667 (1993).
Hegen et al., "Utility of animal models for identification of potential therapeutics for rheumatoid arthritis," Ann. Rheum. Dis., vol. 67, pp. 1505-1515 (2008).
Mueller et al., "Aglycosylated chimeric mouse/human IgG1 antibody retains some effector function," Hybridoma, vol. 10(2), pp. 211-217 (1991) (abstract).
Mueller et al., "Humanized Porcine VCAM-Specific Monoclonal Antibodies With Chimeric IgG2/G4 Constant Regions Block Human Leukocyte Binding to Porcine Endothelial Cells," Molecular Immunology, vol. 34(6), pp. 441-452 (1997).
Rindfleisch et al., "Diagnosis and Management of Rheumatoid Arthritis," American Family Physician, vol. 72(6), pp. 1037-1047 (2005).
Yamaguchi et al., "Application of monoclonal antibody for drug delivery system—Missile therapy for cancer," Nihon Rinsho, vol. 56(3), pp. 638-643 (1998).
Yamaguchi et al., "Application of tumor marker for immunotargeting therapy of cancer," Nihon Rinsho, vol. 54(6), pp. 1674-1679 (1996).
Yamaguchi et al., "Biological Response Modifier and Missile Cancer Chemotherapy," Biotherapy, vol. 10(4), pp. 605-609 (1996).

* cited by examiner

FL2: scFv-9/HA-biotin/SA-PE
FL1: CD5-FITC
FL3: CD19-PerCP

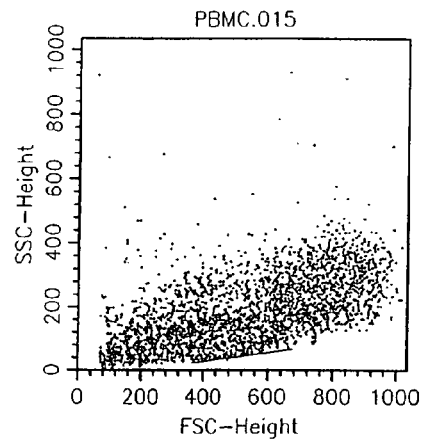

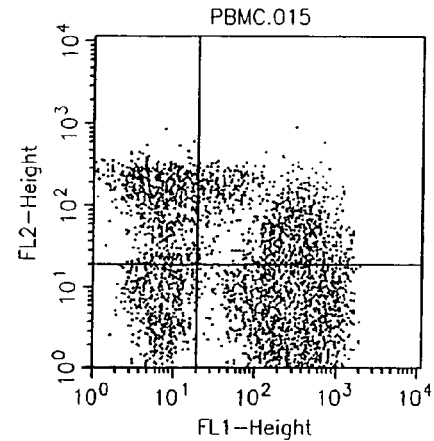

File: PBMC.015
XParameter: FL1-H FL1-Height (Log)
YParameter: FL2-H FL2-Height (Log)

| Quad | Events | %Gated | %Total | XGeo Mean | YGeo Mean |
|------|--------|--------|--------|-----------|-----------|
| UL | 1881 | 9.40 | 5.84 | 6.45 | 118.74 |
| UR | 4368 | 21.84 | 13.56 | 266.89 | 45.49 |
| LL | 2831 | 14.16 | 8.79 | 6.65 | 7.40 |
| LR | 10920 | 54.60 | 33.90 | 282.52 | 5.72 |

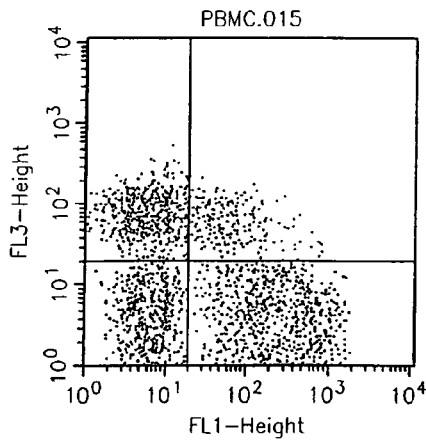

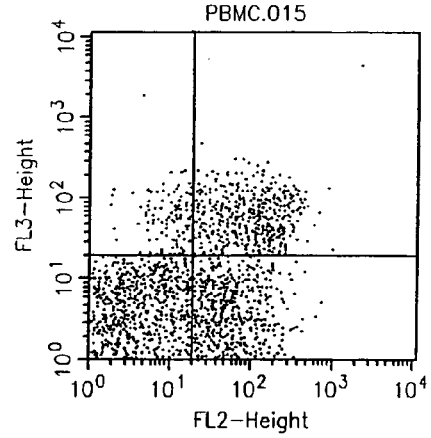

File: PBMC.015
XParameter: FL1-H FL1-Height (Log)
YParameter: FL3-H FL3-Height (Log)

| Quad | Events | %Gated | %Total | XGeo Mean | YGeo Mean |
|------|--------|--------|--------|-----------|-----------|
| UL | 1874 | 9.37 | 5.82 | 6.55 | 65.56 |
| UR | 409 | 2.04 | 1.27 | 50.57 | 55.81 |
| LL | 2838 | 14.19 | 8.81 | 6.57 | 4.19 |
| LR | 14879 | 74.39 | 46.19 | 291.30 | 2.17 |

File: PBMC.015
XParameter: FL2-H FL2-Height (Log)
YParameter: FL3-H FL3-Height (Log)

| Quad | Events | %Gated | %Total | XGeo Mean | YGeo Mean |
|------|--------|--------|--------|-----------|-----------|
| UL | 171 | 0.85 | 0.53 | 10.16 | 54.88 |
| UR | 2112 | 10.56 | 6.56 | 137.20 | 64.47 |
| LL | 13744 | 68.72 | 42.67 | 6.08 | 2.52 |
| LR | 3973 | 19.86 | 12.33 | 41.31 | 2.06 |

*FIG. 7*

Table 1. Summary of CLL scFv Clones

Table 1. CDR Sequence of CLL Specific Rabbit scFv Antibodies

| CLONE | LC-CDR1 | LC-CDR2 | LC-CDR3 |
|---|---|---|---|
| A2c | TLSTGYSVGSYVIA (SEQ ID NO: 1) | HSEEAKHQGS (SEQ ID NO: 18) | ATAHGSGSSFHVV (SEQ ID NO: 25) |
| G12.1c | QASESIRN---YLA (SEQ ID NO: 2) | GASNL----ES (SEQ ID NO: 19) | QSGDYSA---GLT (SEQ ID NO: 26) |
| B4.2a | QASESIRN---YLA (SEQ ID NO: 2) | GASNL----ES (SEQ ID NO: 19) | QSGYYSA---GLT (SEQ ID NO: 27) |
| E1c | QASESISN---WLA (SEQ ID NO: 3) | RASTL----AS (SEQ ID NO: 20) | QSGYYSA---GVT (SEQ ID NO: 28) |
| F2d | QASESISN---YLA (SEQ ID NO: 4) | GASNL----ES (SEQ ID NO: 19) | QSGYYSA---GLT (SEQ ID NO: 27) |
| E5e | QASQNIYS---NLA (SEQ ID NO: 5) | LAFTL----AS (SEQ ID NO: 21) | QGGDYSSSSSYGYG (SEQ ID NO: 29) |
| H6.2b | QASQSVNN---LLA (SEQ ID NO: 6) | GASNL----ES (SEQ ID NO: 19) | QSGYYSP---GVT (SEQ ID NO: 30) |
| G10.1 | QASESINN---YLA (SEQ ID NO: 7) | GASNL----ES (SEQ ID NO: 19) | QSGYYSG---GAT (SEQ ID NO: 31) |
| D11.1c | LASENVYS---AVA (SEQ ID NO: 8) | GASDL----ES (SEQ ID NO: 22) | Q-GYSSYPPT (SEQ ID NO: 32) |
| A5.2c | LASENVYG---AVA (SEQ ID NO: 9) | GASNL----ES (SEQ ID NO: 19) | Q-GYSSYP-T (SEQ ID NO: 33) |
| F1d | QASQSVNN---LLA (SEQ ID NO: 6) | GASNL----ES (SEQ ID NO: 19) | AGYKSSSTD-GIA (SEQ ID NO: 34) |
| F1e | QASQSISN---LLA (SEQ ID NO: 10) | GASNL----ES (SEQ ID NO: 19) | QSGYYSA--GHLT (SEQ ID NO: 35) |
| E4.2 | LASENVAS---TVS (SEQ ID NO: 11) | GASNL----ES (SEQ ID NO: 19) | LGGFGYSTT-GLT (SEQ ID NO: 36) |
| E2c | TLSTGYSVGEYPVV (SEQ ID NO: 12) | HTDDIKHQGS (SEQ ID NO: 23) | AIAHGTESSFHVV (SEQ ID NO: 37) |
| A9c | TLSTGYSVGEYPVV (SEQ ID NO: 12) | HTDDIKHQGS (SEQ ID NO: 23) | AIAHGTESSFHVV (SEQ ID NO: 37) |
| E11e | TLRTGYSVGEYPLV (SEQ ID NO: 13) | HTDDIKHQGS (SEQ ID NO: 23) | ATGHGSGSSAGVV (SEQ ID NO: 38) |
| A1.1 | LASEDIYS---GLS (SEQ ID NO: 14) | GASNL----AS (SEQ ID NO: 19) | LGGYPYSST-GTA (SEQ ID NO: 39) |
| F5.2 | QASQSVNN---LLA (SEQ ID NO: 15) | GASNL----ES (SEQ ID NO: 19) | QSGWYSA--GALT (SEQ ID NO: 40) |
| F10b | QASQSVNN---LLA (SEQ ID NO: 6) | RASTL----AS (SEQ ID NO: 20) | QSGYYRA--GDLT (SEQ ID NO: 41) |
| F7a | QASQSVSN---LLA (SEQ ID NO: 15) | GASNL----ES (SEQ ID NO: 19) | QSGYYSA---GLT (SEQ ID NO: 27) |
| F6b | QASQSVSN---LLA (SEQ ID NO: 15) | GASNL----ES (SEQ ID NO: 19) | QSGYYSA---GLT (SEQ ID NO: 27) |
| C12b | QASQSVSN---LLA (SEQ ID NO: 6) | GASNL----ES (SEQ ID NO: 19) | QSGYYSA--GALT (SEQ ID NO: 42) |
| D2.1b | QASQSVNN---LLA (SEQ ID NO: 16) | GASNL----ES (SEQ ID NO: 19) | QSGYYSA---GLT (SEQ ID NO: 27) |
| D1.1 | QASEDIES---YLA (SEQ ID NO: 16) | GASNL----ES (SEQ ID NO: 19) | QSNAWSV---GMT (SEQ ID NO: 43) |
| D2.2a | QSSQSIAGA-YLS (SEQ ID NO: 17) | LASKL----AS (SEQ ID NO: 24) | AAQYSGN---IYT (SEQ ID NO: 44) |
| D2.2b | LASENVYG---AVA (SEQ ID NO: 9) | GASNL----ES (SEQ ID NO: 19) | Q-GYSSYP-T (SEQ ID NO: 33) |

FIG. 9B

| CLONE | HC-CDR1 | | HC-CDR2 | | HC-CDR3 | |
|---|---|---|---|---|---|---|
| A2c | NYAMT | (SEQ ID NO: 45) | IISNGGA--DYASWAK | (SEQ ID NO: 64) | DDEGYDDYGDYMGYFTL | (SEQ ID NO: 84) |
| G12.1c | SYGLS | (SEQ ID NO: 46) | YFDPVFGNI-YYATWVD | (SEQ ID NO: 65) | DRIYVSSVG----YAFNL | (SEQ ID NO: 85) |
| B4.2a | TYGVS | (SEQ ID NO: 47) | YNDPIFGNT-YYATWVN | (SEQ ID NO: 66) | DRAYASSSG----YXXXX | (SEQ ID NO: 86) |
| E1c | SNAMG | (SEQ ID NO: 48) | IISSSGGT--YYASWAK | (SEQ ID NO: 67) | DWIAAGKS-----YGLDL | (SEQ ID NO: 87) |
| F2d | TNAMG | (SEQ ID NO: 49) | IISSSGST--YYASWAK | (SEQ ID NO: 68) | DWIAAGKS-----YGLDL | (SEQ ID NO: 87) |
| E5e | SSDWIC | (SEQ ID NO: 50) | CIYTGSSSSTWYASWAK | (SEQ ID NO: 69) | RYTGDNG-------NL | (SEQ ID NO: 88) |
| H6.2b | SDVIS | (SEQ ID NO: 51) | YIYTGDGST-DYASWVN | (SEQ ID NO: 70) | DAAYAGYGW----IFNL | (SEQ ID NO: 89) |
| G10.1 | SDVIS | (SEQ ID NO: 51) | YIYTGDGST-DYASWVN | (SEQ ID NO: 70) | DAAYAGYGW----IFNL | (SEQ ID NO: 89) |
| D11.1c | TYAMG | (SEQ ID NO: 52) | SIYASRSP--YYASWAK | (SEQ ID NO: 71) | GDAGSIP------YFKL | (SEQ ID NO: 90) |
| A5.2c | TYAMG | (SEQ ID NO: 52) | SIYASRSP--YYASWAK | (SEQ ID NO: 71) | GDAGSIP------YFKL | (SEQ ID NO: 90) |
| F1d | SNAMT | (SEQ ID NO: 53) | TIIYGDNT--YYASWAK | (SEQ ID NO: 72) | GNV----------FSDL | (SEQ ID NO: 91) |
| F1e | DFAMS | (SEQ ID NO: 54) | VVYAGTRGDTYYANWAK | (SEQ ID NO: 73) | GLT----------YYPL | (SEQ ID NO: 92) |
| E4.2 | DFAMS | (SEQ ID NO: 54) | VVYAGTRGDTYYANWAK | (SEQ ID NO: 73) | GLT----------YYPL | (SEQ ID NO: 92) |
| E2c | SYGMN | (SEQ ID NO: 55) | YIDPDYGST-YYASWVN | (SEQ ID NO: 74) | GAYSGYPS-----YFNL | (SEQ ID NO: 93) |
| A9c | SYGMN | (SEQ ID NO: 55) | YIDPDYGST-YYASWVN | (SEQ ID NO: 74) | GAYSGYPS-----YFNL | (SEQ ID NO: 93) |
| E11e | SNAMS | (SEQ ID NO: 56) | ITYPSGNV--YYASWAK | (SEQ ID NO: 75) | G------------FFNL | (SEQ ID NO: 94) |
| A1.1 | TNAIS | (SEQ ID NO: 57) | YSSYGNNA--HYTNWAK | (SEQ ID NO: 76) | GNA----------YSDL | (SEQ ID NO: 95) |
| F5.2 | SNAMS | (SEQ ID NO: 56) | IIIGSGTT--YYANWAK | (SEQ ID NO: 77) | DQPIIYGAYGDYGLATGTRLDL | (SEQ ID NO: 96) |
| F10b | SYYMS | (SEQ ID NO: 58) | IISSSGTS--YYATWAK | (SEQ ID NO: 78) | DQPIIDAAYGDYGIATGTRLDL | (SEQ ID NO: 97) |
| F7a | SYTMS | (SEQ ID NO: 59) | IISSSGSA--YYATWAK | (SEQ ID NO: 79) | DQPITTDYGGYGIATGTRLDL | (SEQ ID NO: 98) |
| F6b | SNAIS | (SEQ ID NO: 60) | IIVGSGTT--YYADWAK | (SEQ ID NO: 80) | DQPITYAGYGY---ATGTRLDL | (SEQ ID NO: 99) |
| C12b | SNAIS | (SEQ ID NO: 60) | IIVGSGTT--YYADWAK | (SEQ ID NO: 80) | DQPITYAGYGY---ATGTRLDL | (SEQ ID NO: 99) |
| D2.1b | TNAMS | (SEQ ID NO: 61) | TITYGTNA--YYASWAK | (SEQ ID NO: 81) | GNT----------YSDL | (SEQ ID NO: 100) |
| D1.1 | SNAMS | (SEQ ID NO: 56) | TITYGTNA--YYASWAK | (SEQ ID NO: 81) | GNT----------YSDL | (SEQ ID NO: 100) |
| D2.2a | SSYWIC | (SEQ ID NO: 62) | CIYTGSNGSTYYASWAK | (SEQ ID NO: 82) | AYIYGGYG-----FFDL | (SEQ ID NO: 101) |
| D2.2b | NYGVN | (SEQ ID NO: 63) | YIDPVFGST-YYASWVN | (SEQ ID NO: 83) | EASFYY-------GMDL | (SEQ ID NO: 102) |

CLONE: designation of representative clone for sequence; LC: Ig light chain; HC: Ig heavy chain;
CDR: complementarity determining region

FIG. 9B (Cont.)

Table 1(cont'd). Expression Pattern of CLL Specific Rabbit scFv Antibodies

| CLONE | CLL | B | RL | Ramos | TF-1 | Ag | Linker |
|---|---|---|---|---|---|---|---|
| A2c | + | + | ++ | + | - |  | S |
| G12.1c | + | + | + | + | - | CD19 | L |
| B4.2a | + | nd | + | + | - |  | L |
| E1c | ++ | + | - | - | - | CD23 | S |
| F2d | ++ | + | - | - | - |  | S |
| E5e | ± | nd | - | - | - |  | S |
| H6.2b | ++ | ++ | - | - | - |  | S |
| G10.1 | + | + | - | - | - |  | S |
| D11.1c | ++ | + | - | - | - | CD23 | S |
| A5.2c | ++ | + | - | - | - |  | S |
| F1d | + | ± | - | - | - |  | S |
| F1e | ++ | nd | - | - | - |  | S |
| E4.2 | + | + | - | - | - |  | S |
| E2c | + | ± | - | - | - |  | S |
| A9c | ++ | + | - | - | - |  | S |
| E11e | ++ | + | - | - | - |  | S |
| A1.1 | + | + | nd | nd | nd |  | L |
| F5.2 | + | nd | + | + | - |  | L |
| F10b | nd | nd | nd | nd | nd |  | L |
| F7a | nd | nd | nd | nd | nd |  | L |
| F6b | nd | nd | nd | nd | nd |  | L |
| C12b | nd | nd | nd | nd | nd |  | L |
| D2.1b | nd | nd | nd | nd | nd |  | S |
| D1.1 | + | + | nd | nd | nd |  | L |
| D2.2a | nd | nd | nd | nd | nd |  | L |
| D2.2b | nd | nd | nd | nd | nd |  | S |

CLONE: designation of representative clone for sequence
Expression pattern: binding of scFv antibodies to primary human cells and cell lines as determined by whole cell ELISA assay
CLL: chronic lymphocytic leukemias (primary tumors and CLL-AAT cell line)
B: normal, primary human B lymphocytes
RL: non-Hodgkin's lymphoma cell line
Ramos: Burkitt's lymphoma cell line
TF-1: human erythroleukemia cell line
Ag: antigen recognized by scFv antibody (determined by immunoprecipitation and mass spectrometry)
Linker: type of linker sequence between VL and VH regions. S, short linker; L, long linker

*FIG. 9C*

Table 2. Mean fluorescent intensities of B-CLL cells and normal PBMC labeled with scFv antibodies Antibody and CLL/PBMC Ratio:

| Donor | scFv-2 | ratio | scFv-3 | ratio | scFv-6 | ratio | scFv-9 | ratio |
|---|---|---|---|---|---|---|---|---|
| CLL(ML) PBMC-1 | 590 715 | 0.83 | 398 181 | 2.2 | 284 137 | 2.1 | 511 80 | 6.4 |
| CLL(JR) PBMC-2 | 311 368 | 0.85 | 207 87 | 2.4 | nd nd | nd | 117 67 | 1.7 |
| CLL(HTS) PBMC-3 | 219 317 | 0.69 | 173 106 | 1.6 | nd nd | nd | 176 49 | 3.6 |
| CLL(RE) PBMC-4 | 305 513 | 0.59 | 360 121 | 3 | nd nd | nd | 142 81 | 1.7 |
| CLL(GB) PBMC-5 | 262 563 | 0.47 | 387 212 | 1.8 | nd nd | nd | 163 106 | 1.5 |

Primary PBMC from five patients diagnosed with CLL and five normal donors were analyzed by flow cytometry. The geometric mean fluorescent intensities were determined for cells stained with four different scFv antibodies. For scFvs that bind to antigens overexpressed on CLL cells, the CLL/PBMC ratio of fluorescent intensities is >1.0

FIG. 10

Comparison of scFv-9 antigen and CD38 expression on CLL cells.

| Patient ID | %CD19+ | %CD38+ | %scFv-9+ | ScFv-9 Level | CD38 | ScFv-9 |
|---|---|---|---|---|---|---|
| ML | 80 | 40 | 98 | 266 | Hi | Hi |
| IB | 86 | 87 | 96 | 366 | Hi | Hi |
| BH | 76 | 56 | 86 | 284 | Hi | Hi |
| JG | 82 | 92 | 97 | 125 | Hi | Lo |
| RE | 87 | 97 | 100 | 125 | Hi | Lo |
| EM | 91 | 8 | 95 | 268 | Lo | Hi |
| HS | 76 | 11 | 94 | 268 | Lo | Hi |
| MP | 40 | 6 | 95 | 280 | Lo | Hi |
| JR | 81 | 12 | 92 | 124 | Lo | Lo |
| GB | 65 | 20 | 98 | 187 | Lo | Lo |

FIG. 11

Identification of scFv Antigens

- Cell-surface biotinylation (CLL-ATT cells)
- Membrane isolation (nitrogen cavitation, differential centrifugation)
- Immunoprecipitation with scFv-HA coupled to Anti-HA beads
- SDS-PAGE
- Detection by Coomassie-stain or AP-streptavidin Western blot
- MALDI-MS or LC-MS/MS to obtain peptide mass spectra/peptide sequences

SEQUENCE LISTING

<160> NUMBER OF SEQ ID NOS: 102

<210> SEQ ID NO 1
<211> LENGTH: 14
<212> TYPE: PRT
<213> ORGANISM: rabbit

<400> SEQUENCE: 1

Thr Leu Ser Thr Gly Tyr Ser Val Gly Ser Tyr Val Ile Ala
1               5                   10

<210> SEQ ID NO 2
<211> LENGTH: 11
<212> TYPE: PRT
<213> ORGANISM: rabbit

<400> SEQUENCE: 2

Gln Ala Ser Glu Ser Ile Arg Asn Tyr Leu Ala
1               5                   10

<210> SEQ ID NO 3
<211> LENGTH: 11
<212> TYPE: PRT
<213> ORGANISM: rabbit

<400> SEQUENCE: 3

Gln Ala Ser Glu Ser Ile Ser Asn Trp Leu Ala
1               5                   10

<210> SEQ ID NO 4
<211> LENGTH: 11
<212> TYPE: PRT
<213> ORGANISM: rabbit

<400> SEQUENCE: 4

Gln Ala Ser Glu Ser Ile Ser Asn Tyr Leu Ala
1               5                   10

<210> SEQ ID NO 5
<211> LENGTH: 11
<212> TYPE: PRT
<213> ORGANISM: rabbit

<400> SEQUENCE: 5

Gln Ala Ser Gln Asn Ile Tyr Ser Asn Leu Ala
1               5                   10

<210> SEQ ID NO 6
<211> LENGTH: 11
<212> TYPE: PRT
<213> ORGANISM: rabbit

<400> SEQUENCE: 6

Gln Ala Ser Gln Ser Val Asn Asn Leu Leu Ala
1               5                   10

<210> SEQ ID NO 7
<211> LENGTH: 11
<212> TYPE: PRT
<213> ORGANISM: rabbit

<400> SEQUENCE: 7

Gln Ala Ser Glu Ser Ile Asn Asn Tyr Leu Ala
1               5                   10

```
<210> SEQ ID NO 8
<211> LENGTH: 11
<212> TYPE: PRT
<213> ORGANISM: rabbit

<400> SEQUENCE: 8

Leu Ala Ser Glu Asn Val Tyr Ser Ala Val Ala
1               5                   10

<210> SEQ ID NO 9
<211> LENGTH: 11
<212> TYPE: PRT
<213> ORGANISM: rabbit

<400> SEQUENCE: 9

Leu Ala Ser Glu Asn Val Tyr Gly Ala Val Ala
1               5                   10

<210> SEQ ID NO 10
<211> LENGTH: 11
<212> TYPE: PRT
<213> ORGANISM: rabbit

<400> SEQUENCE: 10

Gln Ala Ser Gln Ser Ile Ser Asn Leu Leu Ala
1               5                   10

<210> SEQ ID NO 11
<211> LENGTH: 11
<212> TYPE: PRT
<213> ORGANISM: rabbit

<400> SEQUENCE: 11

Leu Ala Ser Glu Asn Val Ala Ser Thr Val Ser
1               5                   10

<210> SEQ ID NO 12
<211> LENGTH: 14
<212> TYPE: PRT
<213> ORGANISM: rabbit

<400> SEQUENCE: 12

Thr Leu Ser Thr Gly Tyr Ser Val Gly Glu Tyr Pro Val Val
1               5                   10

<210> SEQ ID NO 13
<211> LENGTH: 14
<212> TYPE: PRT
<213> ORGANISM: rabbit

<400> SEQUENCE: 13

Thr Leu Arg Thr Gly Tyr Ser Val Gly Glu Tyr Pro Leu Val
1               5                   10

<210> SEQ ID NO 14
<211> LENGTH: 11
<212> TYPE: PRT
<213> ORGANISM: rabbit

<400> SEQUENCE: 14

Leu Ala Ser Glu Asp Ile Tyr Ser Gly Leu Ser
1               5                   10

<210> SEQ ID NO 15
```

```
<211> LENGTH: 11
<212> TYPE: PRT
<213> ORGANISM: rabbit

<400> SEQUENCE: 15

Gln Ala Ser Gln Ser Val Ser Asn Leu Leu Ala
1               5                   10

<210> SEQ ID NO 16
<211> LENGTH: 11
<212> TYPE: PRT
<213> ORGANISM: rabbit

<400> SEQUENCE: 16

Gln Ala Ser Glu Asp Ile Glu Ser Tyr Leu Ala
1               5                   10

<210> SEQ ID NO 17
<211> LENGTH: 12
<212> TYPE: PRT
<213> ORGANISM: rabbit

<400> SEQUENCE: 17

Gln Ser Ser Gln Ser Ile Ala Gly Ala Tyr Leu Ser
1               5                   10

<210> SEQ ID NO 18
<211> LENGTH: 10
<212> TYPE: PRT
<213> ORGANISM: rabbit

<400> SEQUENCE: 18

His Ser Glu Glu Ala Lys His Gln Gly Ser
1               5                   10

<210> SEQ ID NO 19
<211> LENGTH: 7
<212> TYPE: PRT
<213> ORGANISM: rabbit

<400> SEQUENCE: 19

Gly Ala Ser Asn Leu Glu Ser
1               5

<210> SEQ ID NO 20
<211> LENGTH: 7
<212> TYPE: PRT
<213> ORGANISM: rabbit

<400> SEQUENCE: 20

Arg Ala Ser Thr Leu Ala Ser
1               5

<210> SEQ ID NO 21
<211> LENGTH: 7
<212> TYPE: PRT
<213> ORGANISM: rabbit

<400> SEQUENCE: 21

Leu Ala Phe Thr Leu Ala Ser
1               5

<210> SEQ ID NO 22
<211> LENGTH: 7
<212> TYPE: PRT
<213> ORGANISM: rabbit
```

<400> SEQUENCE: 22

Gly Ala Ser Asp Leu Glu Ser
1               5

<210> SEQ ID NO 23
<211> LENGTH: 10
<212> TYPE: PRT
<213> ORGANISM: rabbit

<400> SEQUENCE: 23

His Thr Asp Asp Ile Lys His Gln Gly Ser
1               5                   10

<210> SEQ ID NO 24
<211> LENGTH: 7
<212> TYPE: PRT
<213> ORGANISM: rabbit

<400> SEQUENCE: 24

Leu Ala Ser Lys Leu Ala Ser
1               5

<210> SEQ ID NO 25
<211> LENGTH: 13
<212> TYPE: PRT
<213> ORGANISM: rabbit

<400> SEQUENCE: 25

Ala Thr Ala His Gly Ser Gly Ser Ser Phe His Val Val
1               5                   10

<210> SEQ ID NO 26
<211> LENGTH: 10
<212> TYPE: PRT
<213> ORGANISM: rabbit

<400> SEQUENCE: 26

Gln Ser Gly Asp Tyr Ser Ala Gly Leu Thr
1               5                   10

<210> SEQ ID NO 27
<211> LENGTH: 10
<212> TYPE: PRT
<213> ORGANISM: rabbit

<400> SEQUENCE: 27

Gln Ser Gly Tyr Tyr Ser Ala Gly Leu Thr
1               5                   10

<210> SEQ ID NO 28
<211> LENGTH: 10
<212> TYPE: PRT
<213> ORGANISM: rabbit

<400> SEQUENCE: 28

Gln Ser Gly Tyr Tyr Ser Ala Gly Val Thr
1               5                   10

<210> SEQ ID NO 29
<211> LENGTH: 14
<212> TYPE: PRT
<213> ORGANISM: rabbit

<400> SEQUENCE: 29

```
Gln Gly Gly Asp Tyr Ser Ser Ser Ser Tyr Gly Tyr Gly
1               5                   10
```

<210> SEQ ID NO 30
<211> LENGTH: 10
<212> TYPE: PRT
<213> ORGANISM: rabbit

<400> SEQUENCE: 30

```
Gln Ser Gly Tyr Tyr Ser Pro Gly Val Thr
1               5                   10
```

<210> SEQ ID NO 31
<211> LENGTH: 10
<212> TYPE: PRT
<213> ORGANISM: rabbit

<400> SEQUENCE: 31

```
Gln Ser Gly Tyr Tyr Ser Gly Gly Ala Thr
1               5                   10
```

<210> SEQ ID NO 32
<211> LENGTH: 9
<212> TYPE: PRT
<213> ORGANISM: rabbit

<400> SEQUENCE: 32

```
Gln Gly Tyr Ser Ser Tyr Pro Pro Thr
1               5
```

<210> SEQ ID NO 33
<211> LENGTH: 8
<212> TYPE: PRT
<213> ORGANISM: rabbit

<400> SEQUENCE: 33

```
Gln Gly Tyr Ser Ser Tyr Pro Thr
1               5
```

<210> SEQ ID NO 34
<211> LENGTH: 12
<212> TYPE: PRT
<213> ORGANISM: rabbit

<400> SEQUENCE: 34

```
Ala Gly Tyr Lys Ser Ser Ser Thr Asp Gly Ile Ala
1               5                   10
```

<210> SEQ ID NO 35
<211> LENGTH: 11
<212> TYPE: PRT
<213> ORGANISM: rabbit

<400> SEQUENCE: 35

```
Gln Ser Gly Tyr Tyr Ser Ala Gly His Leu Thr
1               5                   10
```

<210> SEQ ID NO 36
<211> LENGTH: 12
<212> TYPE: PRT
<213> ORGANISM: rabbit

<400> SEQUENCE: 36

```
Leu Gly Gly Phe Gly Tyr Ser Thr Thr Gly Leu Thr
1               5                   10
```

```
<210> SEQ ID NO 37
<211> LENGTH: 13
<212> TYPE: PRT
<213> ORGANISM: rabbit

<400> SEQUENCE: 37

Ala Ile Ala His Gly Thr Glu Ser Ser Phe His Val Val
1               5                   10

<210> SEQ ID NO 38
<211> LENGTH: 13
<212> TYPE: PRT
<213> ORGANISM: rabbit

<400> SEQUENCE: 38

Ala Thr Gly His Gly Ser Gly Ser Ser Ala Gly Val Val
1               5                   10

<210> SEQ ID NO 39
<211> LENGTH: 12
<212> TYPE: PRT
<213> ORGANISM: rabbit

<400> SEQUENCE: 39

Leu Gly Gly Tyr Pro Tyr Ser Ser Thr Gly Thr Ala
1               5                   10

<210> SEQ ID NO 40
<211> LENGTH: 11
<212> TYPE: PRT
<213> ORGANISM: rabbit

<400> SEQUENCE: 40

Gln Ser Gly Trp Tyr Ser Ala Gly Ala Leu Thr
1               5                   10

<210> SEQ ID NO 41
<211> LENGTH: 11
<212> TYPE: PRT
<213> ORGANISM: rabbit

<400> SEQUENCE: 41

Gln Ser Gly Tyr Tyr Arg Ala Gly Asp Leu Thr
1               5                   10

<210> SEQ ID NO 42
<211> LENGTH: 11
<212> TYPE: PRT
<213> ORGANISM: rabbit

<400> SEQUENCE: 42

Gln Ser Gly Tyr Tyr Ser Ala Gly Ala Leu Thr
1               5                   10

<210> SEQ ID NO 43
<211> LENGTH: 10
<212> TYPE: PRT
<213> ORGANISM: rabbit

<400> SEQUENCE: 43

Gln Ser Asn Ala Trp Ser Val Gly Met Thr
1               5                   10

<210> SEQ ID NO 44
<211> LENGTH: 10
```

```
<212> TYPE: PRT
<213> ORGANISM: rabbit

<400> SEQUENCE: 44

Ala Ala Gln Tyr Ser Gly Asn Ile Tyr Thr
1               5                   10

<210> SEQ ID NO 45
<211> LENGTH: 5
<212> TYPE: PRT
<213> ORGANISM: rabbit

<400> SEQUENCE: 45

Asn Tyr Ala Met Thr
1               5

<210> SEQ ID NO 46
<211> LENGTH: 5
<212> TYPE: PRT
<213> ORGANISM: rabbit

<400> SEQUENCE: 46

Ser Tyr Gly Leu Ser
1               5

<210> SEQ ID NO 47
<211> LENGTH: 5
<212> TYPE: PRT
<213> ORGANISM: rabbit

<400> SEQUENCE: 47

Thr Tyr Gly Val Ser
1               5

<210> SEQ ID NO 48
<211> LENGTH: 5
<212> TYPE: PRT
<213> ORGANISM: rabbit

<400> SEQUENCE: 48

Ser Asn Ala Met Gly
1               5

<210> SEQ ID NO 49
<211> LENGTH: 5
<212> TYPE: PRT
<213> ORGANISM: rabbit

<400> SEQUENCE: 49

Thr Asn Ala Met Gly
1               5

<210> SEQ ID NO 50
<211> LENGTH: 6
<212> TYPE: PRT
<213> ORGANISM: rabbit

<400> SEQUENCE: 50

Ser Ser Asp Trp Ile Cys
1               5

<210> SEQ ID NO 51
<211> LENGTH: 5
<212> TYPE: PRT
<213> ORGANISM: rabbit
```

```
<400> SEQUENCE: 51

Ser Asp Val Ile Ser
1               5

<210> SEQ ID NO 52
<211> LENGTH: 5
<212> TYPE: PRT
<213> ORGANISM: rabbit

<400> SEQUENCE: 52

Thr Tyr Ala Met Gly
1               5

<210> SEQ ID NO 53
<211> LENGTH: 5
<212> TYPE: PRT
<213> ORGANISM: rabbit

<400> SEQUENCE: 53

Ser Asn Ala Met Thr
1               5

<210> SEQ ID NO 54
<211> LENGTH: 5
<212> TYPE: PRT
<213> ORGANISM: rabbit

<400> SEQUENCE: 54

Asp Phe Ala Met Ser
1               5

<210> SEQ ID NO 55
<211> LENGTH: 5
<212> TYPE: PRT
<213> ORGANISM: rabbit

<400> SEQUENCE: 55

Ser Tyr Gly Met Asn
1               5

<210> SEQ ID NO 56
<211> LENGTH: 5
<212> TYPE: PRT
<213> ORGANISM: rabbit

<400> SEQUENCE: 56

Ser Asn Ala Met Ser
1               5

<210> SEQ ID NO 57
<211> LENGTH: 5
<212> TYPE: PRT
<213> ORGANISM: rabbit

<400> SEQUENCE: 57

Thr Asn Ala Ile Ser
1               5

<210> SEQ ID NO 58
<211> LENGTH: 5
<212> TYPE: PRT
<213> ORGANISM: rabbit

<400> SEQUENCE: 58

Ser Tyr Tyr Met Ser
```

<210> SEQ ID NO 59
<211> LENGTH: 5
<212> TYPE: PRT
<213> ORGANISM: rabbit

<400> SEQUENCE: 59

Ser Tyr Thr Met Ser
1               5

<210> SEQ ID NO 60
<211> LENGTH: 5
<212> TYPE: PRT
<213> ORGANISM: rabbit

<400> SEQUENCE: 60

Ser Asn Ala Ile Ser
1               5

<210> SEQ ID NO 61
<211> LENGTH: 5
<212> TYPE: PRT
<213> ORGANISM: rabbit

<400> SEQUENCE: 61

Thr Asn Ala Met Ser
1               5

<210> SEQ ID NO 62
<211> LENGTH: 6
<212> TYPE: PRT
<213> ORGANISM: rabbit

<400> SEQUENCE: 62

Ser Ser Tyr Trp Ile Cys
1               5

<210> SEQ ID NO 63
<211> LENGTH: 5
<212> TYPE: PRT
<213> ORGANISM: rabbit

<400> SEQUENCE: 63

Asn Tyr Gly Val Asn
1               5

<210> SEQ ID NO 64
<211> LENGTH: 15
<212> TYPE: PRT
<213> ORGANISM: rabbit

<400> SEQUENCE: 64

Ile Ile Ser Ser Asn Gly Gly Ala Asp Tyr Ala Ser Trp Ala Lys
1               5                   10                  15

<210> SEQ ID NO 65
<211> LENGTH: 16
<212> TYPE: PRT
<213> ORGANISM: rabbit

<400> SEQUENCE: 65

Tyr Phe Asp Pro Val Phe Gly Asn Ile Tyr Tyr Ala Thr Trp Val Asp
1               5                   10                  15

```
<210> SEQ ID NO 66
<211> LENGTH: 16
<212> TYPE: PRT
<213> ORGANISM: rabbit

<400> SEQUENCE: 66

Tyr Asn Asp Pro Ile Phe Gly Asn Thr Tyr Tyr Ala Thr Trp Val Asn
1               5                   10                  15

<210> SEQ ID NO 67
<211> LENGTH: 15
<212> TYPE: PRT
<213> ORGANISM: rabbit

<400> SEQUENCE: 67

Ile Ile Ser Ser Ser Gly Gly Thr Tyr Tyr Ala Ser Trp Ala Lys
1               5                   10                  15

<210> SEQ ID NO 68
<211> LENGTH: 15
<212> TYPE: PRT
<213> ORGANISM: rabbit

<400> SEQUENCE: 68

Ile Ile Ser Ser Ser Gly Ser Thr Tyr Tyr Ala Ser Trp Ala Lys
1               5                   10                  15

<210> SEQ ID NO 69
<211> LENGTH: 17
<212> TYPE: PRT
<213> ORGANISM: rabbit

<400> SEQUENCE: 69

Cys Ile Tyr Thr Gly Ser Ser Ser Thr Trp Tyr Ala Ser Trp Ala
1               5                   10                  15

Lys

<210> SEQ ID NO 70
<211> LENGTH: 16
<212> TYPE: PRT
<213> ORGANISM: rabbit

<400> SEQUENCE: 70

Tyr Ile Tyr Thr Gly Asp Gly Ser Thr Asp Tyr Ala Ser Trp Val Asn
1               5                   10                  15

<210> SEQ ID NO 71
<211> LENGTH: 15
<212> TYPE: PRT
<213> ORGANISM: rabbit

<400> SEQUENCE: 71

Ser Ile Tyr Ala Ser Arg Ser Pro Tyr Tyr Ala Ser Trp Ala Lys
1               5                   10                  15

<210> SEQ ID NO 72
<211> LENGTH: 15
<212> TYPE: PRT
<213> ORGANISM: rabbit

<400> SEQUENCE: 72

Thr Ile Ile Tyr Gly Asp Asn Thr Tyr Tyr Ala Ser Trp Ala Lys
1               5                   10                  15

<210> SEQ ID NO 73
```

```
<211> LENGTH: 17
<212> TYPE: PRT
<213> ORGANISM: rabbit

<400> SEQUENCE: 73

Val Val Tyr Ala Gly Thr Arg Gly Asp Thr Tyr Tyr Ala Asn Trp Ala
1               5                   10                  15

Lys

<210> SEQ ID NO 74
<211> LENGTH: 16
<212> TYPE: PRT
<213> ORGANISM: rabbit

<400> SEQUENCE: 74

Tyr Ile Asp Pro Asp Tyr Gly Ser Thr Tyr Tyr Ala Ser Trp Val Asn
1               5                   10                  15

<210> SEQ ID NO 75
<211> LENGTH: 15
<212> TYPE: PRT
<213> ORGANISM: rabbit

<400> SEQUENCE: 75

Ile Thr Tyr Pro Ser Gly Asn Val Tyr Tyr Ala Ser Trp Ala Lys
1               5                   10                  15

<210> SEQ ID NO 76
<211> LENGTH: 15
<212> TYPE: PRT
<213> ORGANISM: rabbit

<400> SEQUENCE: 76

Tyr Ser Ser Tyr Gly Asn Asn Ala His Tyr Thr Asn Trp Ala Lys
1               5                   10                  15

<210> SEQ ID NO 77
<211> LENGTH: 15
<212> TYPE: PRT
<213> ORGANISM: rabbit

<400> SEQUENCE: 77

Ile Ile Ile Gly Ser Gly Thr Thr Tyr Tyr Ala Asn Trp Ala Lys
1               5                   10                  15

<210> SEQ ID NO 78
<211> LENGTH: 15
<212> TYPE: PRT
<213> ORGANISM: rabbit

<400> SEQUENCE: 78

Ile Ile Ser Ser Ser Gly Thr Ser Tyr Tyr Ala Thr Trp Ala Lys
1               5                   10                  15

<210> SEQ ID NO 79
<211> LENGTH: 15
<212> TYPE: PRT
<213> ORGANISM: rabbit

<400> SEQUENCE: 79

Ile Ile Ser Ser Ser Gly Ser Ala Tyr Tyr Ala Thr Trp Ala Lys
1               5                   10                  15

<210> SEQ ID NO 80
<211> LENGTH: 15
```

```
<212> TYPE: PRT
<213> ORGANISM: rabbit

<400> SEQUENCE: 80

Ile Ile Val Gly Ser Gly Thr Thr Tyr Tyr Ala Asp Trp Ala Lys
1               5                   10                  15

<210> SEQ ID NO 81
<211> LENGTH: 15
<212> TYPE: PRT
<213> ORGANISM: rabbit

<400> SEQUENCE: 81

Thr Ile Thr Tyr Gly Thr Asn Ala Tyr Tyr Ala Ser Trp Ala Lys
1               5                   10                  15

<210> SEQ ID NO 82
<211> LENGTH: 17
<212> TYPE: PRT
<213> ORGANISM: rabbit

<400> SEQUENCE: 82

Cys Ile Tyr Thr Gly Ser Asn Gly Ser Thr Tyr Tyr Ala Ser Trp Ala
1               5                   10                  15

Lys

<210> SEQ ID NO 83
<211> LENGTH: 16
<212> TYPE: PRT
<213> ORGANISM: rabbit

<400> SEQUENCE: 83

Tyr Ile Asp Pro Val Phe Gly Ser Thr Tyr Tyr Ala Ser Trp Val Asn
1               5                   10                  15

<210> SEQ ID NO 84
<211> LENGTH: 17
<212> TYPE: PRT
<213> ORGANISM: rabbit

<400> SEQUENCE: 84

Asp Asp Glu Gly Tyr Asp Asp Tyr Gly Asp Tyr Met Gly Tyr Phe Thr
1               5                   10                  15

Leu

<210> SEQ ID NO 85
<211> LENGTH: 14
<212> TYPE: PRT
<213> ORGANISM: rabbit

<400> SEQUENCE: 85

Asp Arg Ile Tyr Val Ser Ser Val Gly Tyr Ala Phe Asn Leu
1               5                   10

<210> SEQ ID NO 86
<211> LENGTH: 14
<212> TYPE: PRT
<213> ORGANISM: rabbit
<220> FEATURE:
<221> NAME/KEY: MISC_FEATURE
<222> LOCATION: (11)..(14)
<223> OTHER INFORMATION: Xaa = is an unknown amino acid

<400> SEQUENCE: 86

Asp Arg Ala Tyr Ala Ser Ser Ser Gly Tyr Xaa Xaa Xaa Xaa
```

<210> SEQ ID NO 87
<211> LENGTH: 13
<212> TYPE: PRT
<213> ORGANISM: rabbit

<400> SEQUENCE: 87

Asp Trp Ile Ala Ala Gly Lys Ser Tyr Gly Leu Asp Leu
1               5                   10

<210> SEQ ID NO 88
<211> LENGTH: 9
<212> TYPE: PRT
<213> ORGANISM: rabbit

<400> SEQUENCE: 88

Arg Tyr Thr Gly Asp Asn Gly Asn Leu
1               5

<210> SEQ ID NO 89
<211> LENGTH: 13
<212> TYPE: PRT
<213> ORGANISM: rabbit

<400> SEQUENCE: 89

Asp Ala Ala Tyr Ala Gly Tyr Gly Trp Ile Phe Asn Leu
1               5                   10

<210> SEQ ID NO 90
<211> LENGTH: 11
<212> TYPE: PRT
<213> ORGANISM: rabbit

<400> SEQUENCE: 90

Gly Asp Ala Gly Ser Ile Pro Tyr Phe Lys Leu
1               5                   10

<210> SEQ ID NO 91
<211> LENGTH: 7
<212> TYPE: PRT
<213> ORGANISM: rabbit

<400> SEQUENCE: 91

Gly Asn Val Phe Ser Asp Leu
1               5

<210> SEQ ID NO 92
<211> LENGTH: 7
<212> TYPE: PRT
<213> ORGANISM: rabbit

<400> SEQUENCE: 92

Gly Leu Thr Tyr Tyr Pro Leu
1               5

<210> SEQ ID NO 93
<211> LENGTH: 12
<212> TYPE: PRT
<213> ORGANISM: rabbit

<400> SEQUENCE: 93

Gly Ala Tyr Ser Gly Tyr Pro Ser Tyr Phe Asn Leu
1               5                   10

```
<210> SEQ ID NO 94
<211> LENGTH: 5
<212> TYPE: PRT
<213> ORGANISM: rabbit

<400> SEQUENCE: 94

Gly Phe Phe Asn Leu
1               5

<210> SEQ ID NO 95
<211> LENGTH: 7
<212> TYPE: PRT
<213> ORGANISM: rabbit

<400> SEQUENCE: 95

Gly Asn Ala Tyr Ser Asp Leu
1               5

<210> SEQ ID NO 96
<211> LENGTH: 22
<212> TYPE: PRT
<213> ORGANISM: rabbit

<400> SEQUENCE: 96

Asp Gln Pro Ile Ile Tyr Gly Ala Tyr Gly Asp Tyr Gly Leu Ala Thr
1               5                   10                  15

Gly Thr Arg Leu Asp Leu
            20

<210> SEQ ID NO 97
<211> LENGTH: 22
<212> TYPE: PRT
<213> ORGANISM: rabbit

<400> SEQUENCE: 97

Asp Gln Pro Ile Ile Asp Ala Ala Tyr Gly Asp Tyr Gly Ile Ala Thr
1               5                   10                  15

Gly Thr Arg Leu Asp Leu
            20

<210> SEQ ID NO 98
<211> LENGTH: 22
<212> TYPE: PRT
<213> ORGANISM: rabbit

<400> SEQUENCE: 98

Asp Gln Pro Ile Ile Thr Thr Asp Tyr Gly Gly Tyr Gly Ile Ala Thr
1               5                   10                  15

Gly Thr Arg Leu Asp Leu
            20

<210> SEQ ID NO 99
<211> LENGTH: 19
<212> TYPE: PRT
<213> ORGANISM: rabbit

<400> SEQUENCE: 99

Asp Gln Pro Ile Thr Tyr Ala Gly Tyr Gly Tyr Ala Thr Gly Thr Arg
1               5                   10                  15

Leu Asp Leu

<210> SEQ ID NO 100
<211> LENGTH: 7
<212> TYPE: PRT
```

```
<213> ORGANISM: rabbit

<400> SEQUENCE: 100

Gly Asn Thr Tyr Ser Asp Leu
1               5

<210> SEQ ID NO 101
<211> LENGTH: 13
<212> TYPE: PRT
<213> ORGANISM: rabbit

<400> SEQUENCE: 101

Ala Tyr Ile Tyr Tyr Gly Gly Tyr Gly Phe Phe Asp Leu
1               5                   10

<210> SEQ ID NO 102
<211> LENGTH: 10
<212> TYPE: PRT
<213> ORGANISM: rabbit

<400> SEQUENCE: 102

Glu Ala Ser Phe Tyr Tyr Gly Met Asp Leu
1               5                   10
```

CHRONIC LYMPHOCYTIC LEUKEMIA CELL LINE

RELATED APPLICATIONS

This application is a continuation of U.S. application Ser. No. 10/379,151, filed Mar. 4, 2003 now U.S. Pat. No. 7,435,412 which is a continuation in part of PCT/US01/47931 filed on Dec. 10, 2001 which is an international application that claims priority to U.S. Provisional Application No. 60/254,113 filed Dec. 8, 2000. The entire disclosures of the aforementioned applications are incorporated herein by reference.

TECHNICAL FIELD

Cell lines derived from chronic lymphocytic leukemia (CLL) cells and the uses thereof in the study and treatment of CLL disease are disclosed. In particular, this disclosure relates to a CLL cell line designated "CLL-AAT", deposited on Dec. 11, 2001 with the American Type Culture Collection (Manassas, Va., USA) in accordance with the terms of the Budapest Treaty under ATCC accession no. PTA-3920.

BACKGROUND

Chronic Lymphocytic Leukemia (CLL) is a disease of the white blood cells and is the most common form of leukemia in the Western Hemisphere. CLL represents a diverse group of diseases relating to the growth of malignant lymphocytes that grow slowly but have an extended life span. CLL is classified in various categories that include, for example, B-cell chronic lymphocytic leukemia (B-CLL) of classical and mixed types, B-cell and T-cell prolymphocytic leukemia, hairy cell leukemia, and large granular lymphocytic leukemia.

Of all the different types of CLL, B-CLL accounts for approximately 30 percent of all leukemias. Although it occurs more frequently in individuals over 50 years of age it is increasingly seen in younger people. B-CLL is characterized by accumulation of B-lymphocytes that are morphologically normal but biologically immature, leading to a loss of function. Lymphocytes normally function to fight infection. In B-CLL, however, lymphocytes accumulate in the blood and bone marrow and cause swelling of the lymph nodes. The production of normal bone marrow and blood cells is reduced and patients often experience severe anemia as well as low platelet counts. This can pose the risk of life-threatening bleeding and the development of serious infections because of reduced numbers of white blood cells.

To further understand diseases such as leukemia it is important to have suitable cell lines that can be used as tools for research on their etiology, pathogenesis and biology. Examples of malignant human B-lymphoid cell lines include pre-B acute lymphoblasticleukemia (Reh), diffuse large cell lymphoma (WSU-DLCL2), and Waldenstrom's macroglobulinemia (WSU-WM). Unfortunately, many of the existing cell lines do not represent the clinically most common types of leukemia and lymphoma.

The use of Epstein Barr Virus (EBV) infection in vitro has resulted in some CLL derived cell lines, in particular B-CLL cells lines, that are representative of the malignant cells. The phenotype of these cell lines is different than that of the in vivo tumors and instead the features of B-CLL lines tend to be similar to those of Lymphoblastoid cell lines. Attempts to immortalize B-CLL cells with the aid of EBV infection have had little success. The reasons for this are unclear but it is known that it is not due a lack of EBV receptor expression, binding or uptake. Wells et al. found that B-CLL cells were arrested in the G1/S phase of the cell cycle and that transformation associated EBV DNA was not expressed. This suggests that the interaction of EBV with B-CLL cells is different from that with normal B cells. EBV-transformed CLL cell lines moreover appear to differentiate, possessing a morphology more similar to lymphoblastoid cell lines (LCL) immortalized by EBV.

An EBV-negative CLL cell line, WSU-CLL, has been established previously (Mohammad et al., (1996) Leukemia 10(1):130-7). However, no other such cell lines are known.

There remains a need in the art, therefore, for a CLL cell line which has not been established by transformation with EBV, and which expresses surface markers characteristic of primary CLL cells.

SUMMARY

In one embodiment an CLL cell line of malignant origin is provided that is not established by immortalisation with EBV. The cell line, which was derived from primary CLL cells, and is deposited under ATCC accession no. PTA-3920. In a preferred embodiment, the cell line is CLL-AAT. CLL-AAT is B-CLL cell line, derived from a B-CLL primary cell.

In a further aspect, the CLL-AAT cell line is used to generate monoclonal antibodies useful in the diagnosis and/or treatment of CLL. Antibodies may be generated by using the cells as disclosed herein as immunogens, thus raising an immune response in animals from which monoclonal antibodies may be isolated. The sequence of such antibodies may be determined and the antibodies or variants thereof produced by recombinant techniques. In this aspect, "variants" includes chimeric, CDR-grafted, humanized and fully human antibodies based on the sequence of the monoclonal antibodies.

Moreover, antibodies derived from recombinant libraries ("phage antibodies") may be selected using the cells described herein, or polypeptides derived therefrom, as bait to isolate the antibodies on the basis of target specificity.

In a still further aspect, antibodies may be generated by panning antibody libraries using primary CLL cells, or antigens derived therefrom, and further screened and/or characterized using a CLL cell line, such as, for example, the CLL cell line described herein. Accordingly, a method for characterizing an antibody specific for CLL is provided, which includes assessing the binding of the antibody to a CLL cell line.

In a further aspect, there is provided a method for identifying proteins uniquely expressed in CLL cells employing the CLL-AAT cell line, by methods well known to those, skilled with art, such as by immunoprecipitation followed by mass spectroscopy analyses. Such proteins may be uniquely expressed in the CLL-AAT cell line, or in primary cells derived from CLL patients.

Small molecule libraries (many available commercially) may be screened using the CLL-AAT cell line in a cell-based assay to identify agents capable of modulating the growth characteristics of the cells. For example, the agents may be identified which modulate apoptosis in the CLL-AAT cell line, or which inhibit growth and/or proliferation thereof. Such agents are candidates for the development of therapeutic compounds.

Nucleic acids isolated from CLL-AAT cell lines may be used in subtractive hybridization experiments to identify CLL-specific genes or in micro array analyses (e.g., gene chip experiments). Genes whose transcription is modulated in CLL cells may be identified. Polypeptide or nucleic acid gene products identified in this manner are useful as leads for the development of antibody or small molecule therapies for CLL.

In a preferred aspect, the CLL-AAT cell line may be used to identify internalizing antibodies, which bind to cell surface components which are internalized by the cell. Such antibodies are candidates for therapeutic use. In particular, single-chain antibodies, which remain stable in the cytoplasm and which retain intracellular binding activity, may be screened in this manner.

In yet another aspect, a therapeutic treatment is described in which a patient is screened for the presence of a polypeptide that is upregulated by a malignant cancer cell and an antibody that interferes with the metabolic pathway of the upregulated polypeptide is administered to the patient.

BRIEF DESCRIPTION OF THE FIGURES

FIG. 7 shows the binding specificity of scFv antibodies in accordance with this disclosure as analyzed by 3-color flow cytometry. In normal peripheral blood mononuclear cells, the antigen recognized by scFv-9 is moderately expressed on B lymphocytes and weakly expressed on a subpopulation of T lymphocytes. PBMC from a normal donor were analyzed by 3-color flow cytometry using anti-CD5-FITC, anti-CD19-PerCP, and scFv-9/Anti-HA-biotin/streptavidin-PE.

FIGS. 9a-9c provide a summary of CDR sequences and binding specificities of selected scFv antibodies. As shown in FIG. 9b, the clone numbers listed in the left column are also referred to herein by scFv numbers as follows: A2c (scFv-1), G12.1c (scFv-2), B4.2a (scFv-17), E1c (scFv-3), F2d (scFv-18), E5e (scFv-4), H6.2b (scFv-5), G10.1 (scFv-19), D11.1c (scFv-6), A5.2c (scFv-20), F1d (scFv-7), F1e (scFv-8), E4.2 (scFv-21), E2c (scFv-9), A9c (scFv-9), E11e (scFv-10), A1.1 (scFv-11), F5.2 (scFv-12), F10b (scFv-22), F7a (scFv-23), F6b (scFv-13), C12b (scFv-24), D2.1b (scFv-14), D1.1 (scFv-25), D2.2a (scFv-15), and D2.2b (scFv-16).

FIG. 10. is Table 2 which shows a summary of flow cytometry results comparing expression levels of scFv antigens on primary CLL cells vs. normal PBMC as described in FIGS. 8a-8c.

FIG. 11. is a Table showing a summary of flow cytometry results comparing expression levels of scFv-9 antigen with the percentage of CD38+ cells in peripheral blood mononuclear cells isolated from ten CLL patients.

DETAILED DESCRIPTION

Definitions

Figure 1:
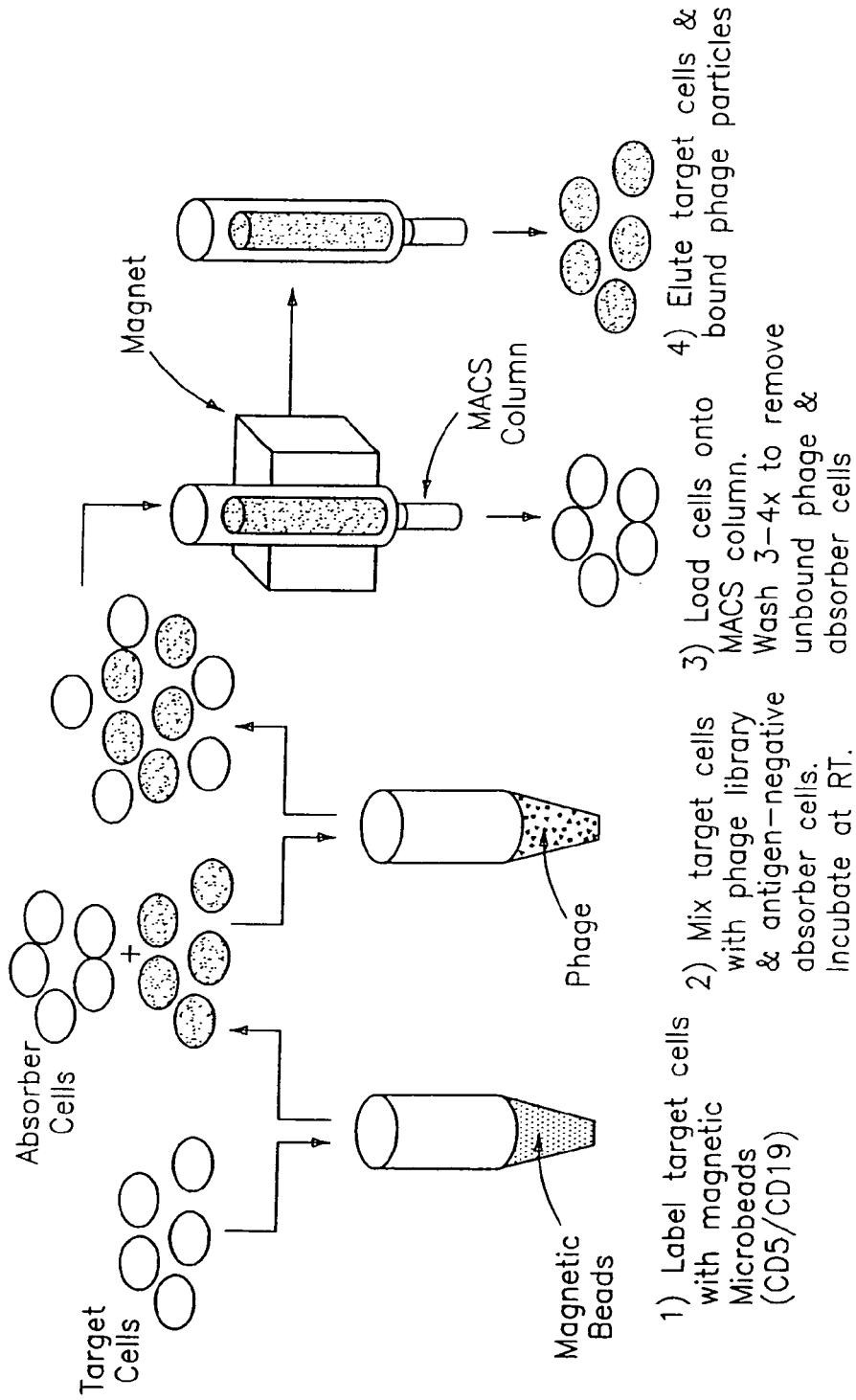
FIG. 1. schematically illustrates typical steps involved in cell surface panning of antibody libraries by magnetically-activated cell sorting (MACS).
Figure 2:
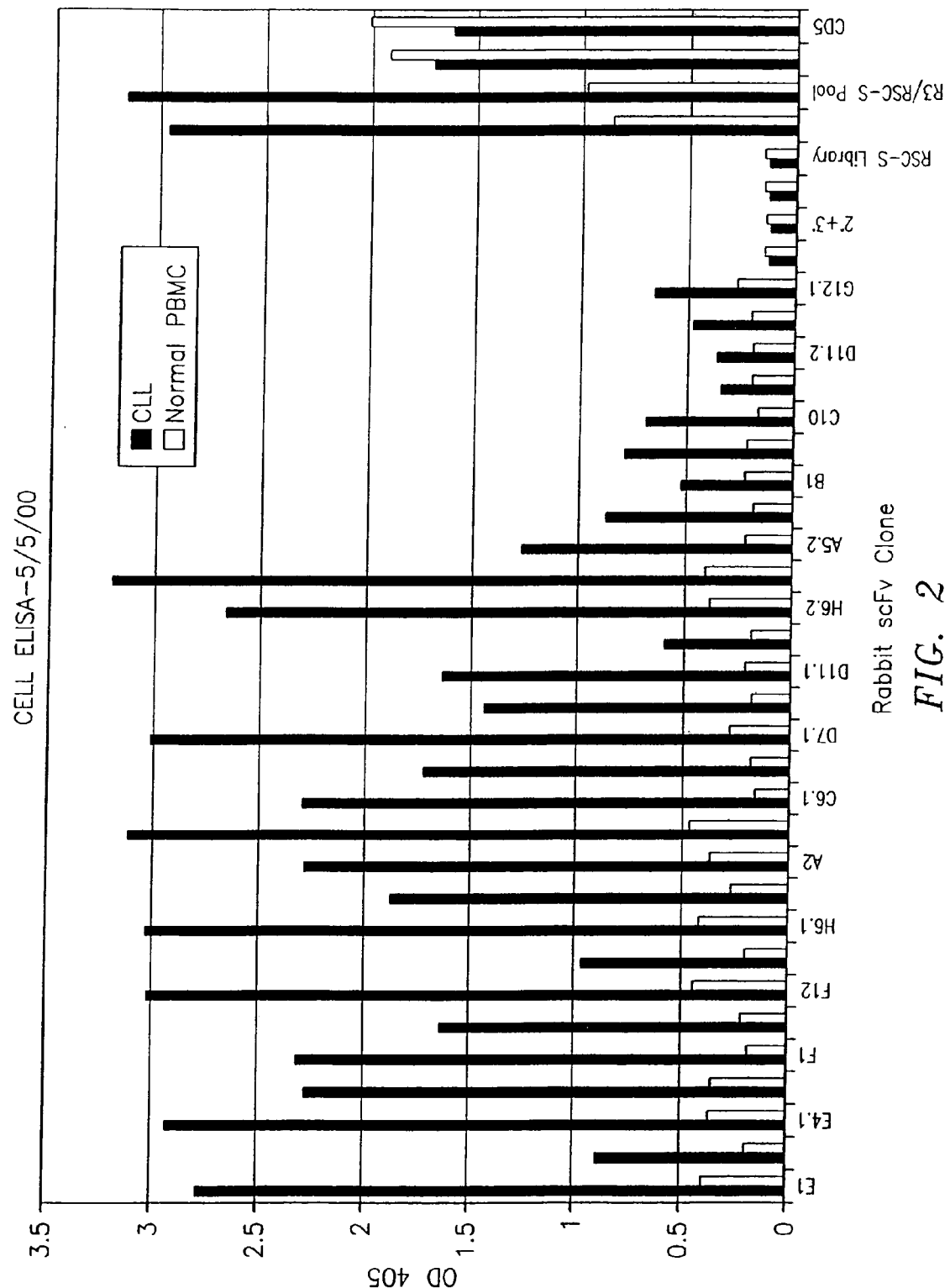
FIG. 2. is a graph showing the results of whole cell ELISA demonstrating binding of selected scFv clones to primary B-CLL cells and absence of binding to normal human PBMC. The designation 2°+3° in this and other figures refers to negative control wells stained with Mouse Anti-HA and detecting antimouse antibodies alone. The designation RSC-S Library in this and other figures refers to soluble antibodies prepared from original rabbit scFv unpanned library. The designation R3/RSC-S Pool in this and other figures refers to soluble antibodies prepared from entire pool of scFv antibodies from round 3 of panning. Anti-CD5 antibody was used as a positive control to verify that equal numbers of B-CLL and PBMC cells were plated in each well.
Figure 3A:
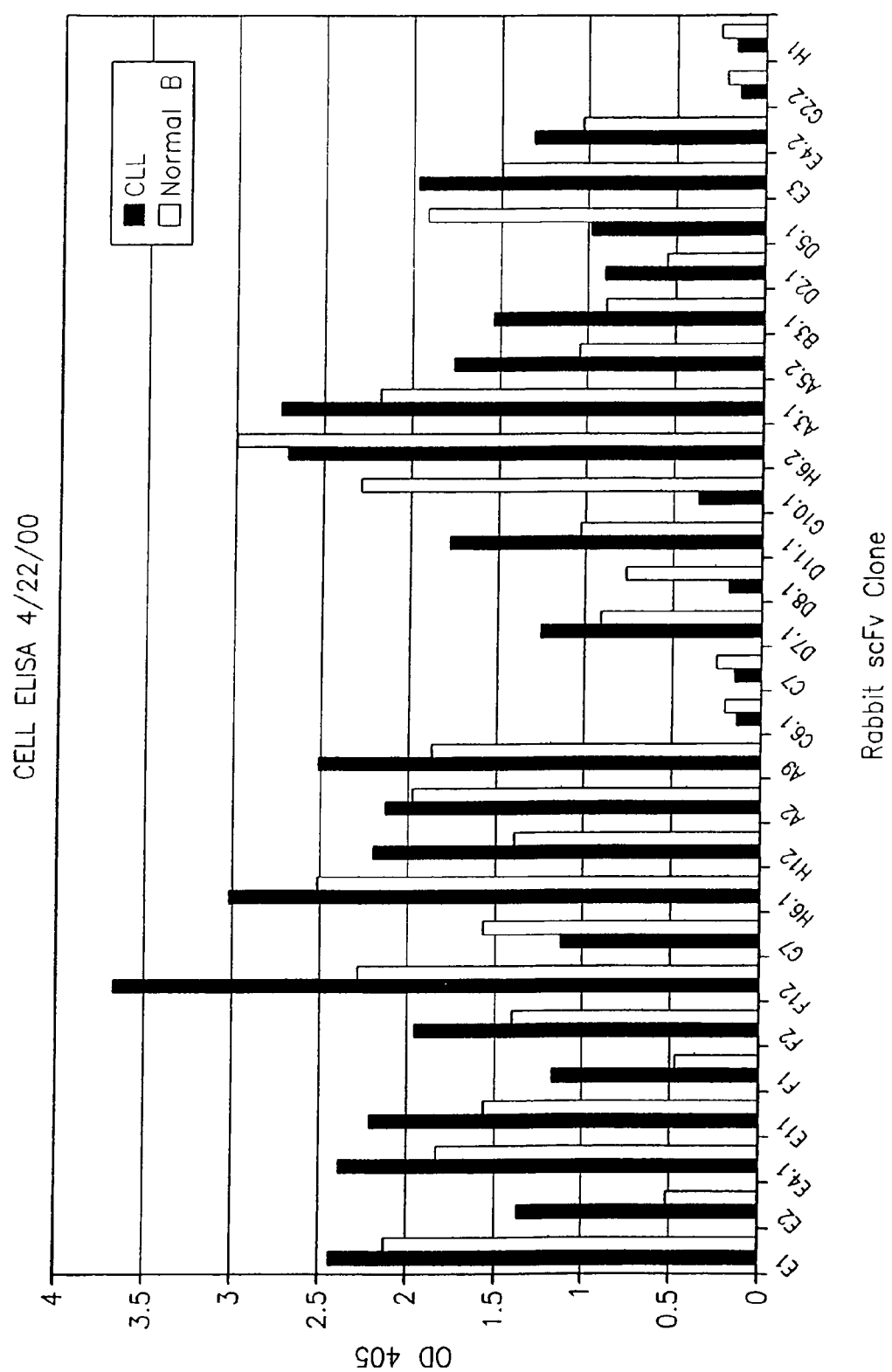
FIGS. 3a and 3b show the results of whole cell ELISA comparing binding of selected scFv antibodies to primary B-CLL cells and normal primary human B cells. Anti-CD19 antibody was used as a positive control to verify that equal numbers of B-CLL and normal B cells were plated in each well. Other controls were as described in the legend to FIG. 2.
Figure 3B:
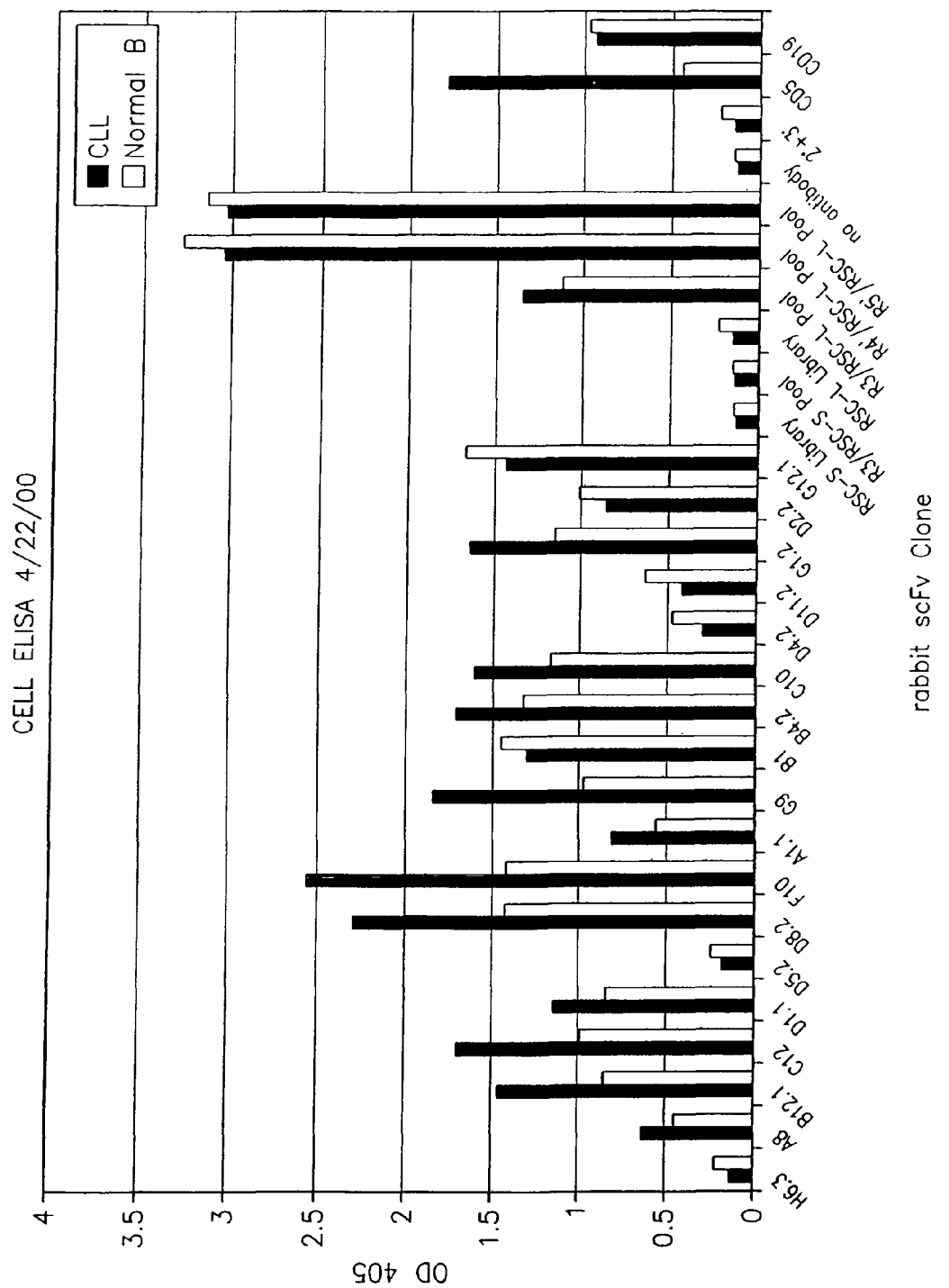
Figure 4A:
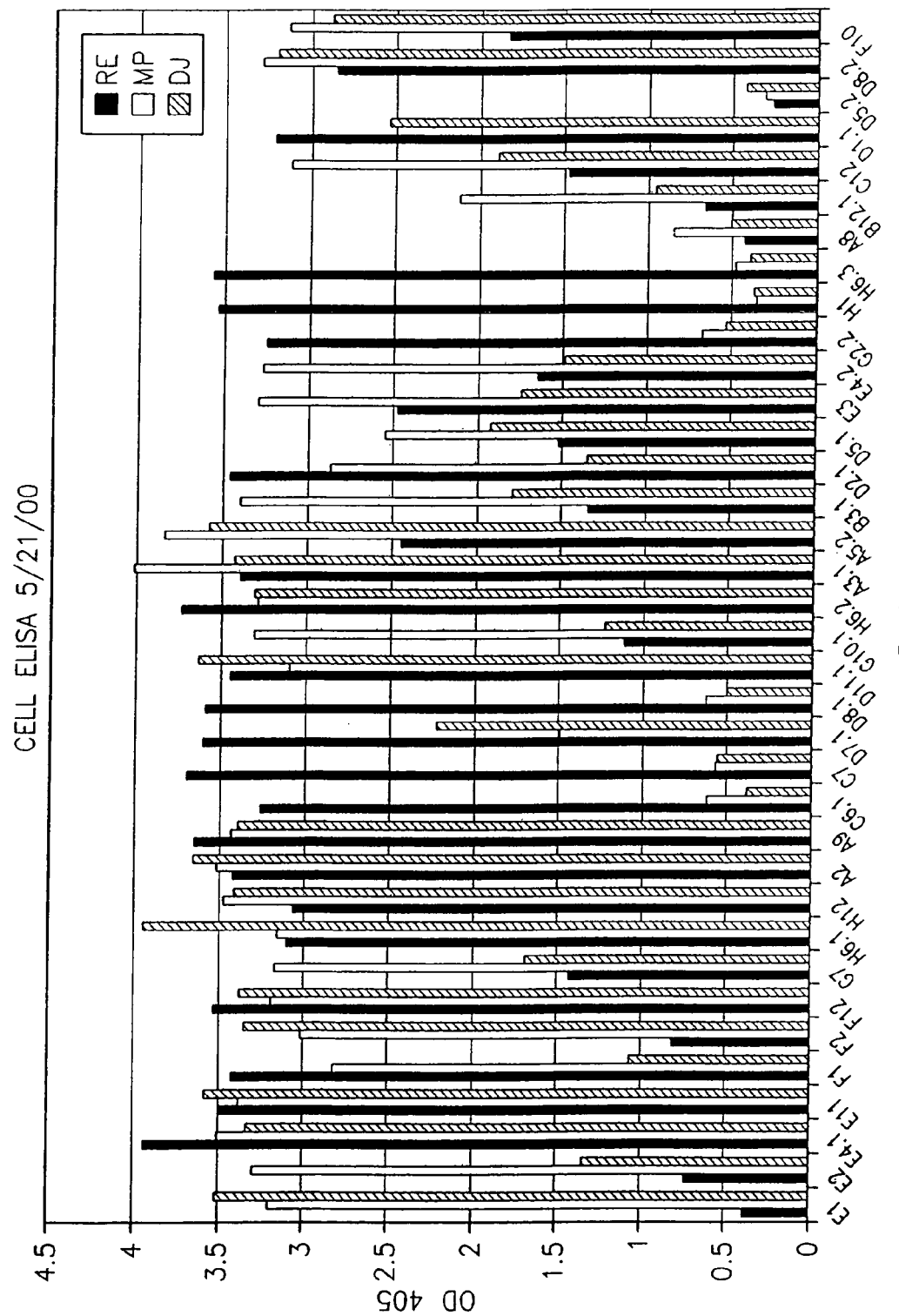
FIGS. 4a and 4b show the results of whole cell ELISA used to determine if scFv clones bind to patient-specific (i.e. idiotype) or blood type-specific (i.e. HLA) antigens. Each clone was tested for binding to PBMC isolated from 3 different B-CLL patients. Clones that bound to patient sample were considered to be patient or blood type-specific.
Figure 4B:
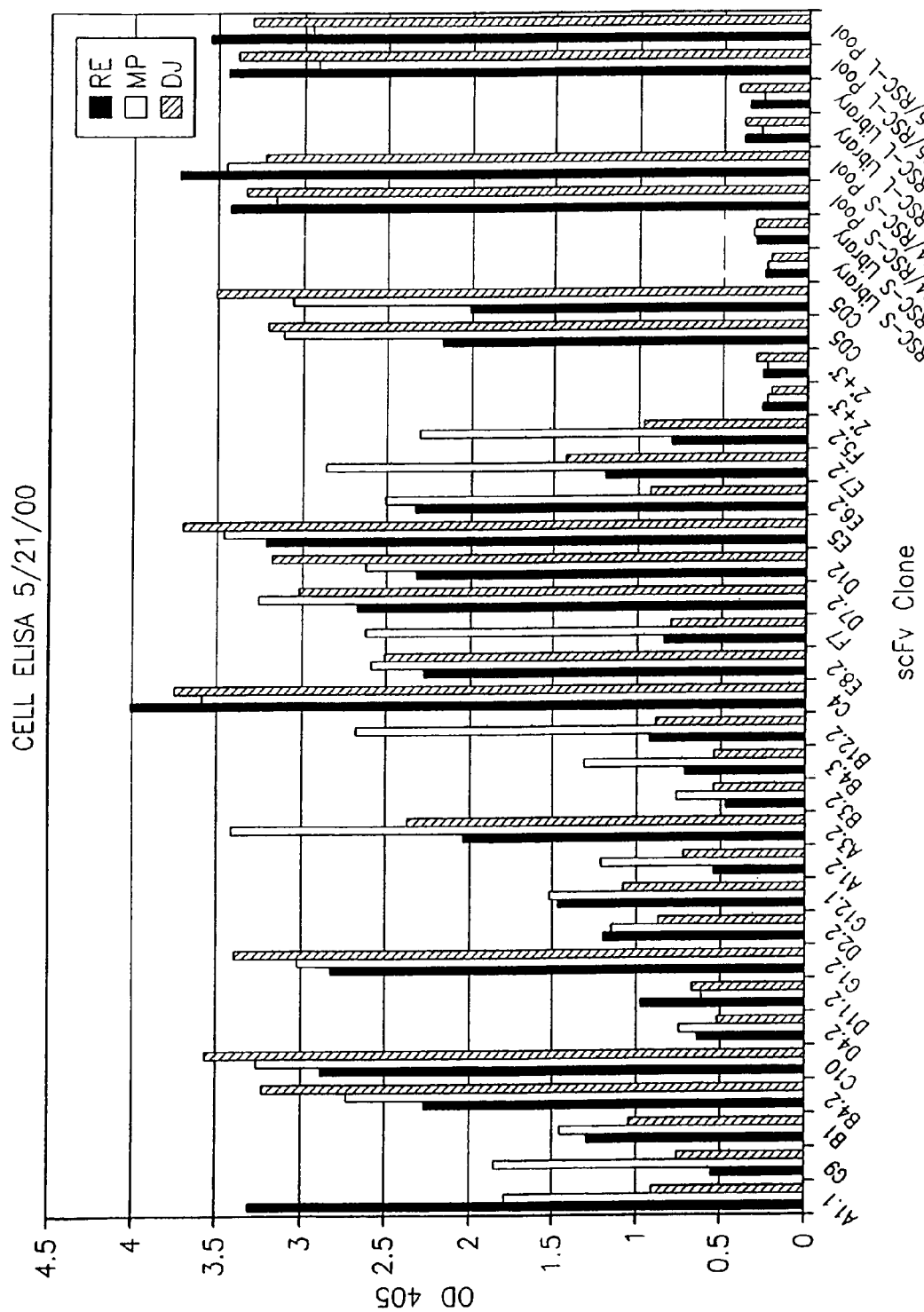
Figure 5A:
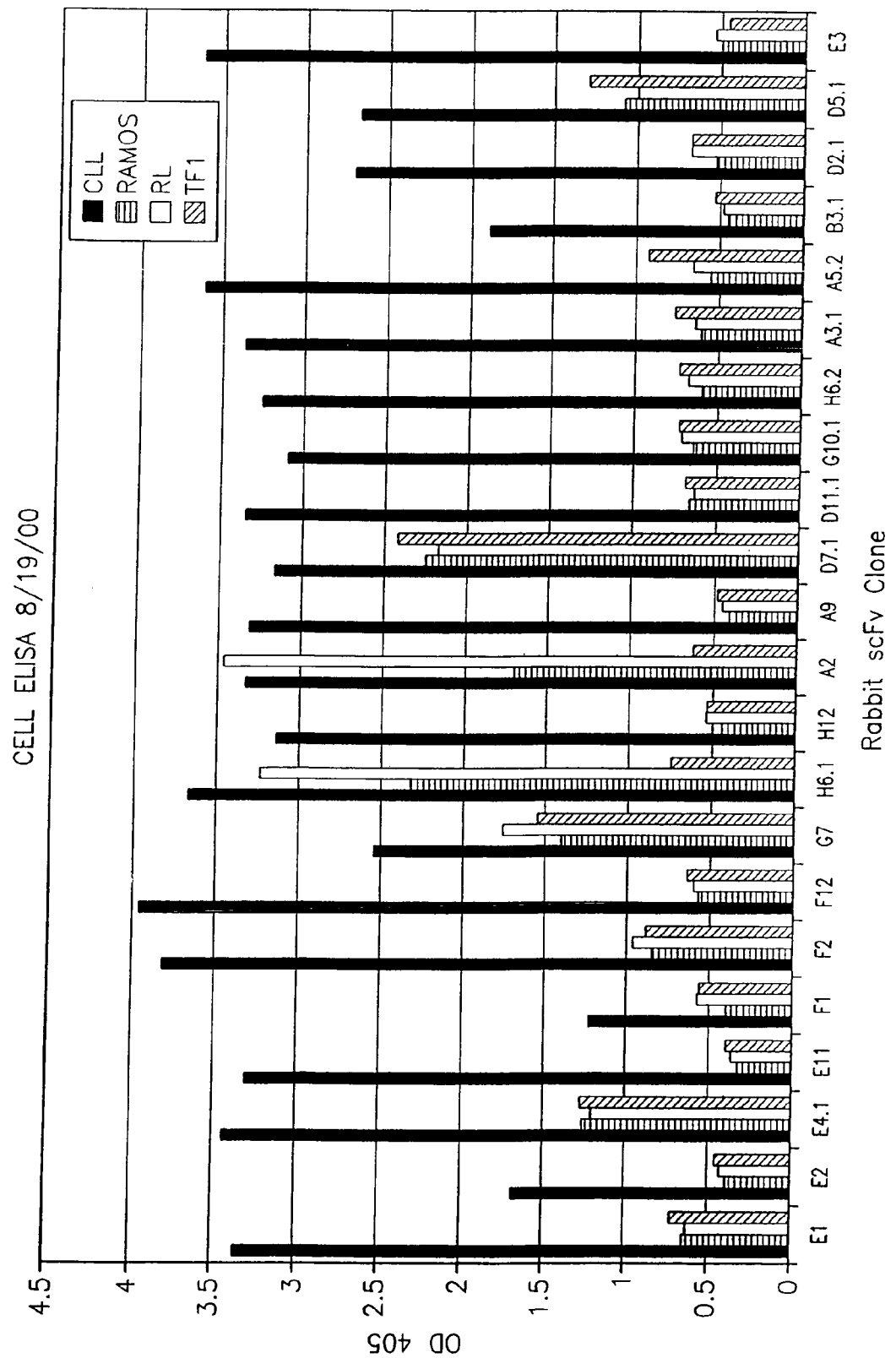
FIGS. 5a and 5b show the results of whole cell ELISA comparing binding of scFv clones to primary B-CLL cells and three human leukemic cell lines. Ramos is a mature B cell line derived from a Burkitt's lymphoma. RL is a mature B cell line derived from a non-Hodgkin's lymphoma. TF-I is an erythroblastoid cell line derived from a erythroleukemia.
Figure 5B:
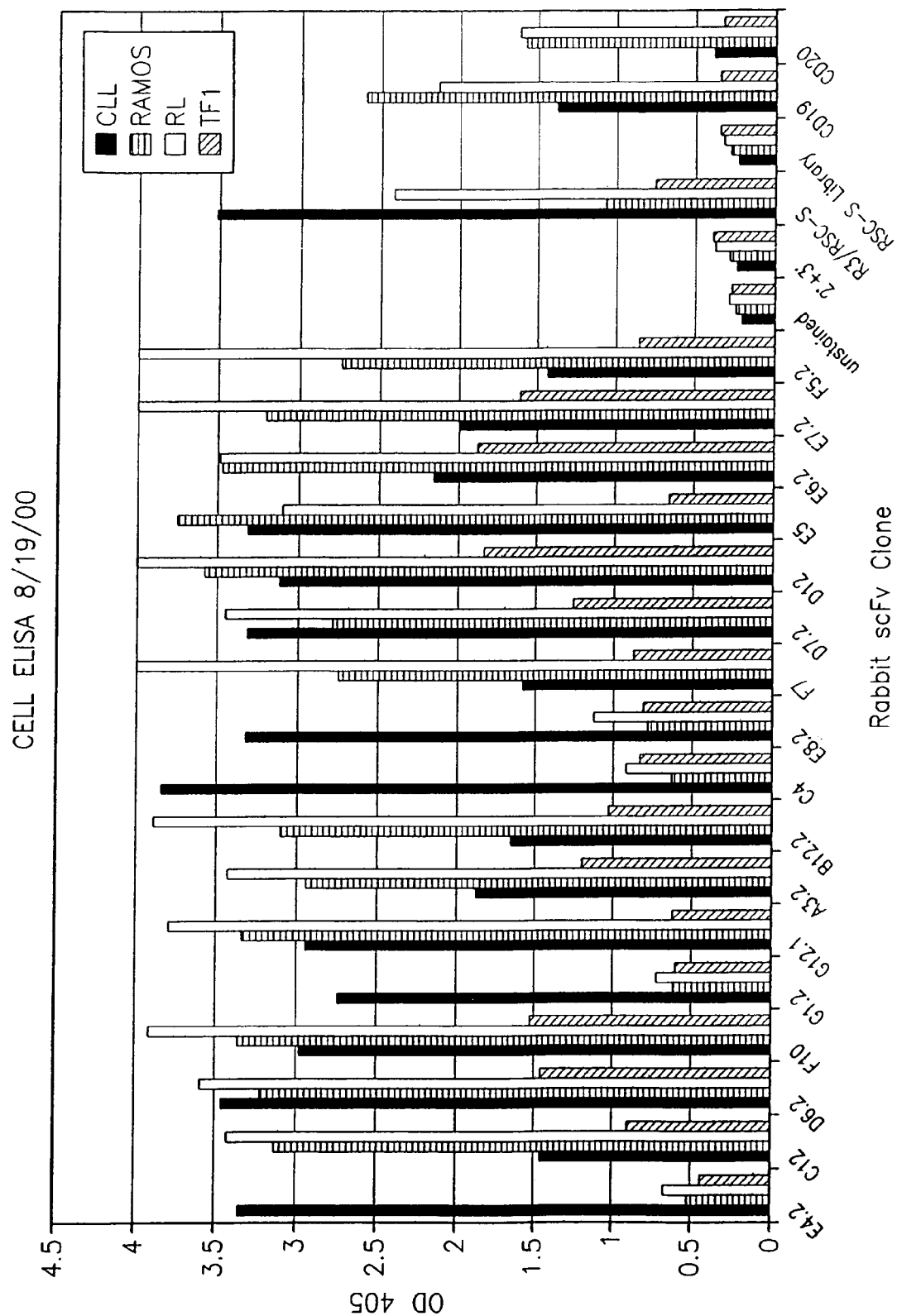
Figure 6A:
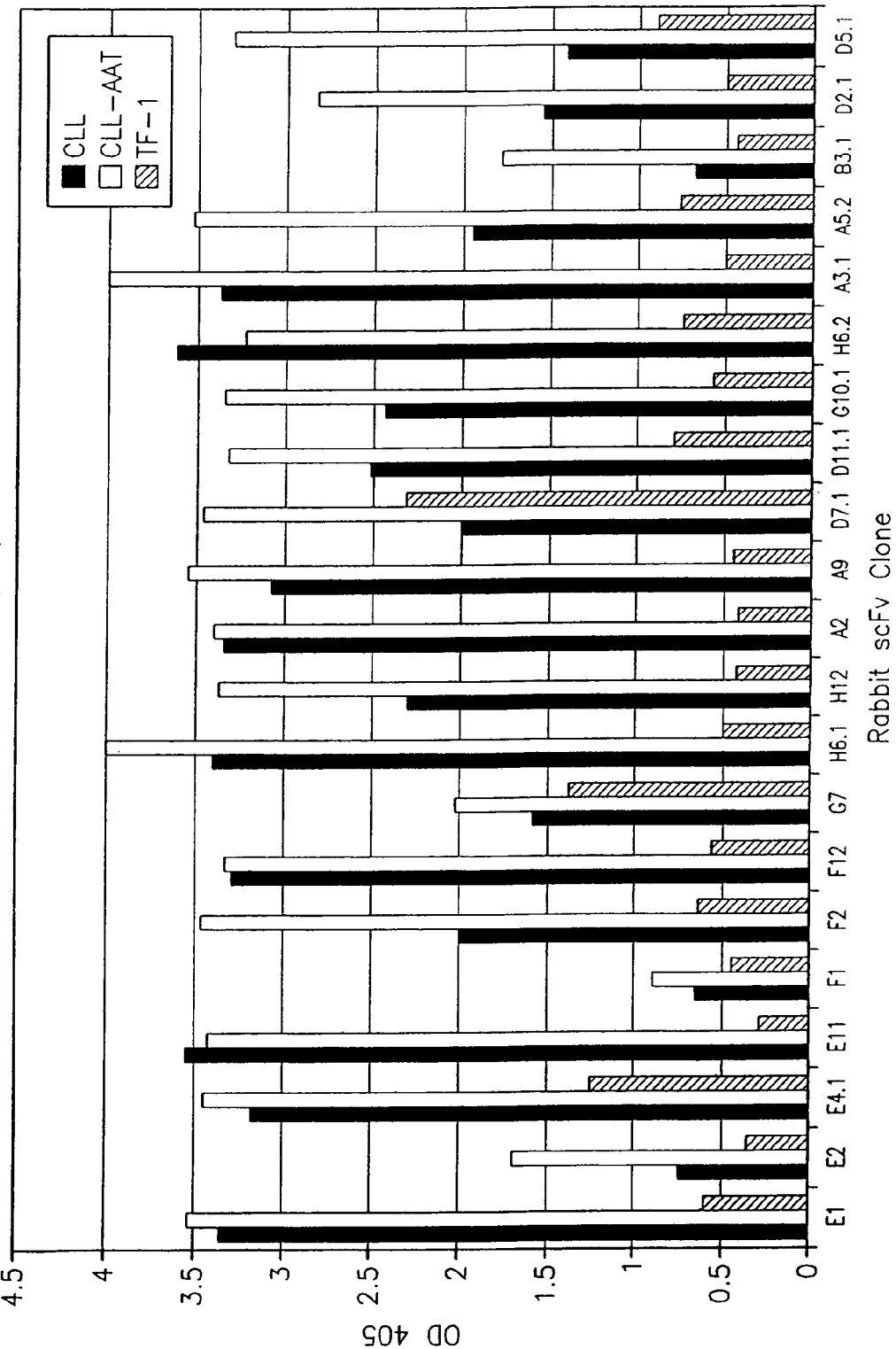
FIGS. 6a, 6b and 6c show the results of whole cell ELISA comparing binding of scFv clones to primary B-CLL cells and CLL-AAT, a cell line derived from a B-CLL is patient. TF-I cells were included as a negative control.
Figure 6B:
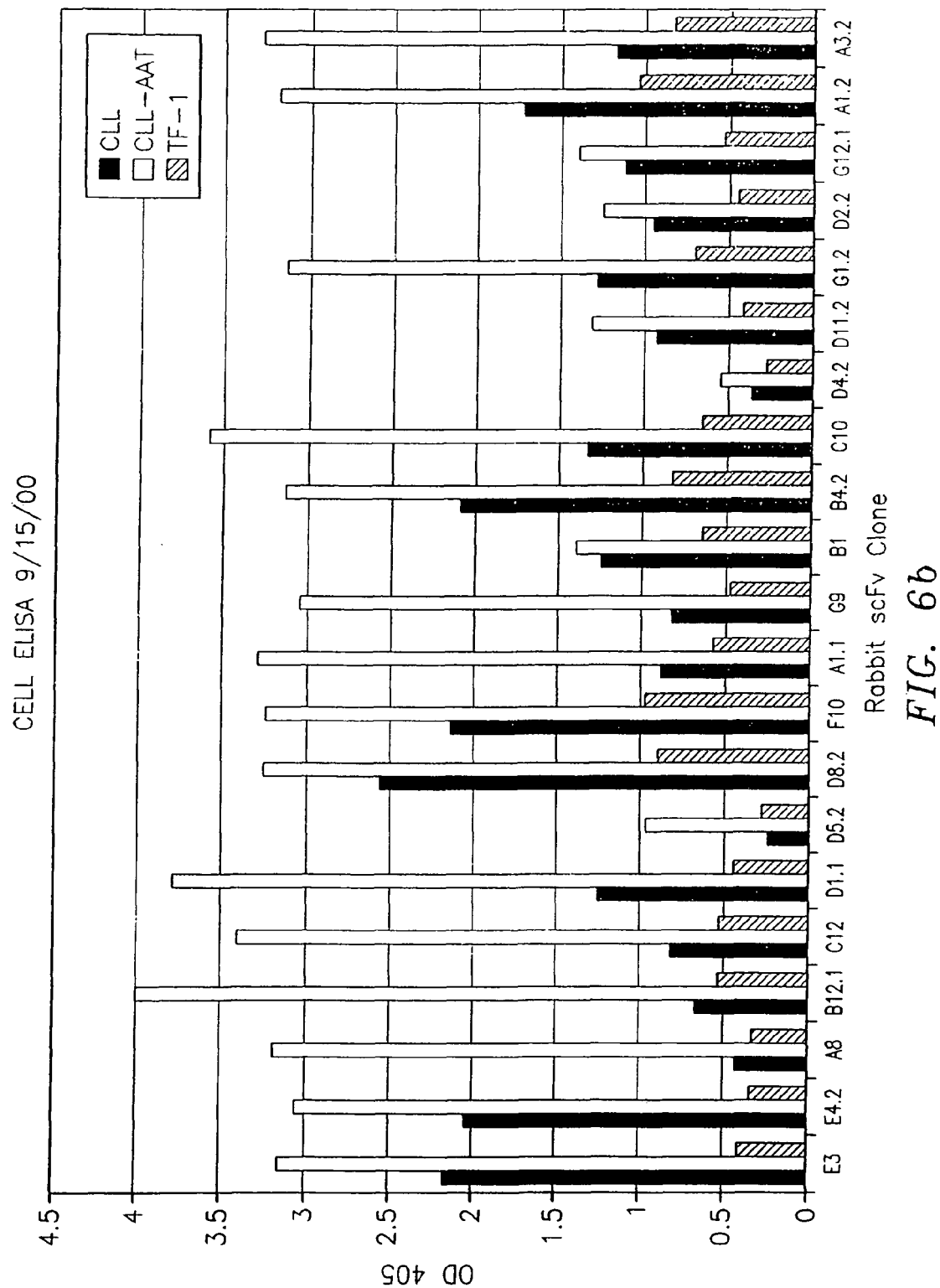
Figure 6C:
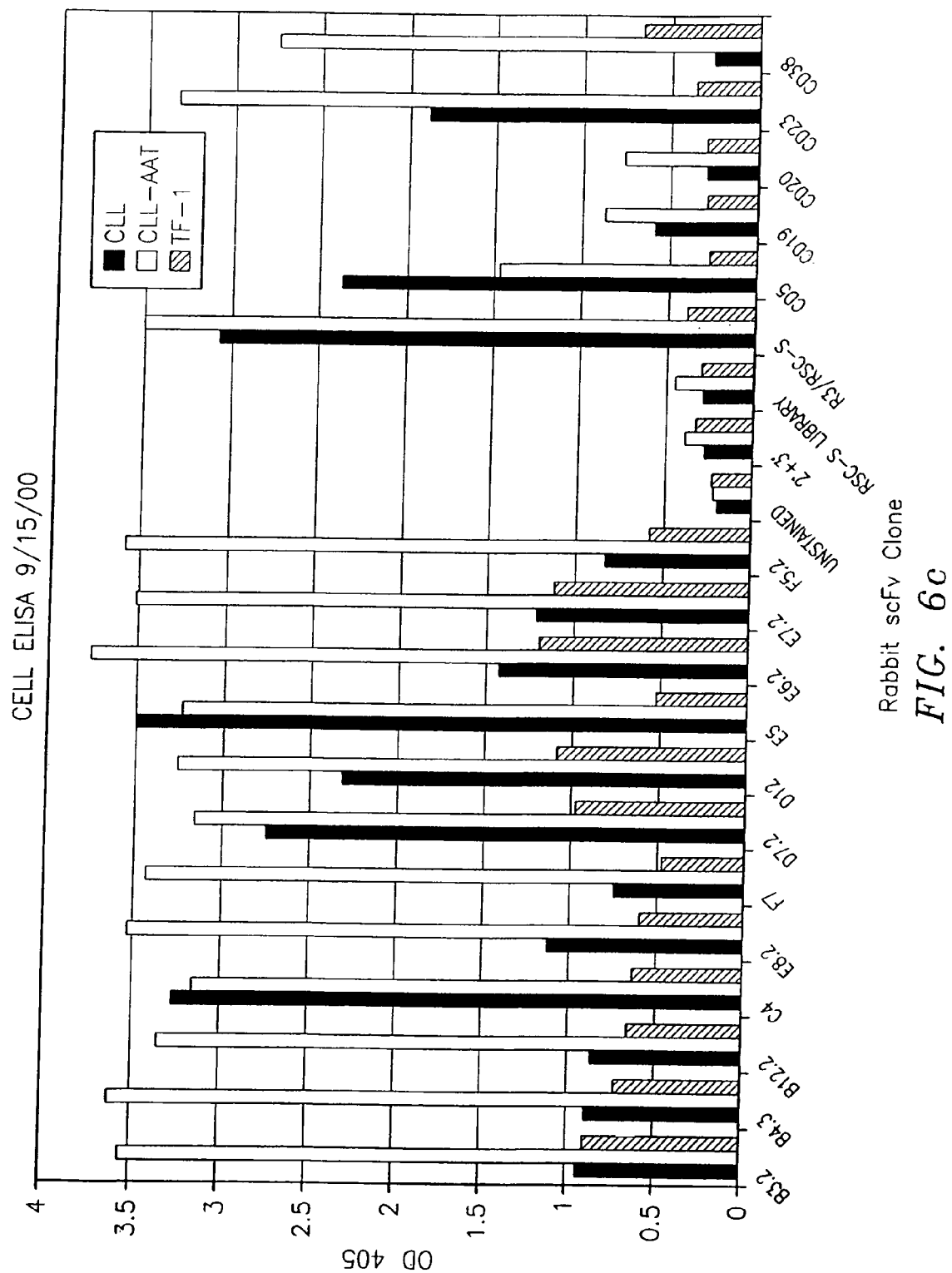

"CLL", as used herein, refers to chronic lymphocytic leukemia involving any lymphocyte, including but not limited to various developmental stages of B cells and T cells, including but not limited to B cell CLL. B-CLL, as used herein, refers to leukemia with a mature B cell phenotype which is CD5$^+$, CD23$^+$, CD2O$^{dim+}$, sIg$^{dim+}$ and arrested in GO/G1 of the cell cycle.

"Malignant origin" refers to the derivation of the cell line from malignant CLL primary cells, as opposed to non-proliferating cells which are transformed, for example, with EBV. Cell lines according to this disclosure may be themselves malignant in phenotype, or not. A CLL cell having a "malignant" phenotype encompasses cell growth unattached from substrate media characterized by repeated cycles of cell growth and exhibits resistance to apoptosis.

Preparation of Cell Lines

Cell lines may be produced according to established methodologies known to those skilled in the art. In general, cell lines are produced by culturing primary cells derived from a patient until immortalized cells are spontaneously generated in culture. These cells are then isolated and further cultured, to produce clonal cell populations or cells exhibiting resistance to apoptosis.

For example, CLL cells may be isolated from peripheral blood drawn from a patient suffering from CLL. The cells may be washed, and optionally immunotyped in order to determine the type(s) of cells present. Subsequently, the cells may be cultured in a medium, such as a medium containing IL-4. Advantageously, all or part of the medium is replaced one or more times during the culture process. Cell lines may be isolated thereby, and will be identified by increased growth in culture.

Preparation of Monoclonal Antibodies

Antibodies, as used herein, refers to complete antibodies or antibody fragments capable of binding to a selected target. Included are Fv, ScFv, Fab' and F(ab')2, monoclonal and polyclonal antibodies, engineered antibodies (including chimeric, CDR-grafted and humanized, fully human antibodies, and artificially selected antibodies), and synthetic or semi synthetic antibodies produced using phage display or alternative techniques. Small fragments, such Fv and ScFv, possess advantageous properties for diagnostic and therapeutic applications on account of their small size and consequent superior tissue distribution.

The antibodies are especially indicated for diagnostic and therapeutic applications. Accordingly, they may be altered antibodies comprising an effector protein such as a toxin or a label. Especially preferred are labels which allow the imaging of the distribution of the antibody in vivo. Such labels may be radioactive labels or radiopaque labels, such as metal particles, which are readily visualisable within the body of a patient. Moreover, the labels may be fluorescent labels or other labels which are visualisable on tissue samples removed from patients.

Recombinant DNA technology may be used to improve the antibodies produced in accordance with this disclosure. Thus, chimeric antibodies may be constructed in order to decrease the immunogenicity thereof in diagnostic or therapeutic applications. Moreover, immunogenicity may be minimized by humanizing the antibodies by CDR grafting and, optionally, framework modification. See, U.S. Pat. No. 5,225,539, the contents of which are incorporated herein by reference.

Antibodies may be obtained from animal serum, or, in the case of monoclonal antibodies or fragments thereof produced in cell culture. Recombinant DNA technology may be used to produce the antibodies according to established procedure, in bacterial or preferably mammalian cell culture. The selected cell culture system preferably secretes the antibody product.

In another embodiment, a process for the production of an antibody disclosed herein includes culturing a host, e.g. *E. coli* or a mammalian cell, which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to polycistronic, for example bicistronic, DNA sequences encoding antibody proteins each individually operably linked to a signal peptide in the proper reading frame.

Multiplication of hybridoma cells or mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal to exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NLYM, NZM, Terrific Broth, SOB, SOC, 2×YT, or M9 Minimal Medium. For yeast, suitable culture media include medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast, plant, or mammalian cell cultivation are known in the art and include homogeneous suspension culture (e.g. in an airlift reactor or in a continuous stirrer reactor), and immobilized or entrapped cell culture (e.g. in hollow fibres, microcapsules, on agarose microbeads or ceramic cartridges).

Large quantities of the desired antibodies can also be obtained by multiplying mammalian cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristine. After one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, the disclosures of which are all incorporated herein by reference. Techniques for the preparation of recombinant antibody molecules is described in the above references and also in, for example WO97/08320; U.S. Pat. No. 5,427,908; U.S. Pat. No. 5,508, 717; Smith, 1985, Science, Vol. 225, pp 1315-1317; Parmley and Smith 1988, Gene 73, pp 305-318; De La Cruz et al, 1988, Journal of Biological Chemistry, 263 pp 4318-4322; U.S. Pat. No. 5,403,484; U.S. Pat. No. 5,223,409; WO88/06630; WO92/15679; U.S. Pat. No. 5,780,279; U.S. Pat. No. 5,571, 698; U.S. Pat. No. 6,040,136; Davis et al., Cancer Metastasis Rev., 1999; 18(4):421-5; Taylor, et al., Nucleic Acids Research 20 (1992): 6287-6295; Tomizuka et al., Proc. Nat.

Academy of Sciences USA 97(2) (2000): 722-727. The contents of all these references are incorporated herein by reference.

The cell culture supernatants are screened for the desired antibodies, preferentially by immunofluorescent staining of CLL cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with a one or more surface polypeptides derived from a CLL cell line according to this disclosure, or with Protein-A or G.

Another embodiment provides a process for the preparation of a bacterial cell line secreting antibodies directed against the cell line characterized in that a suitable mammal, for example a rabbit, is immunized with pooled CLL patient samples. A phage display library produced from the immunized rabbit is constructed and panned for the desired antibodies in accordance with methods well known in the art (such as, for example, the methods disclosed in the various references incorporated herein by reference).

Hybridoma cells secreting the monoclonal antibodies are also contemplated. The preferred hybridoma cells are genetically stable, secrete monoclonal antibodies described herein of the desired specificity and can be activated from deep-frozen cultures by thawing and recloning.

In another embodiment, a process is provided for the preparation of a hybridoma cell line secreting monoclonal antibodies directed to the CLL cell line is described herein. In that process, a suitable mammal, for example a Balb/c mouse, is immunized with a one or more polypeptides or antigenic fragments thereof derived from a cell described in this disclosure, the cell line itself, or an antigenic carrier containing a purified polypeptide as described. Antibody-producing cells of the immunized mammal are grown briefly in culture or fused with cells of a suitable myeloma cell line. The hybrid cells obtained in the fusion are cloned, and cell clones secreting the desired antibodies are selected. For example, spleen cells of Balb/c mice immunized with the present cell line are fused with cells of the myeloma cell line PAI or the myeloma cell line Sp2/0-Ag 14, the obtained hybrid cells are screened for secretion of the desired antibodies, and positive hybridoma cells are cloned.

Preferred is a process for the preparation of a hybridoma cell line, characterized in that Balb/c mice are immunized by injecting subcutaneously and/or intraperitoneally between $10^6$ and $10^7$ cells of a cell line in accordance with this disclosure several times, e.g. four to six times, over several months, e.g. between two and four months. Spleen cells from the immunized mice are taken two to four days after the last injection and fused with cells of the myeloma cell line PAI in the presence of a fusion promoter, preferably polyethylene glycol. Preferably, the myeloma cells are fused with a three- to twenty-fold excess of spleen cells from the immunized mice in a solution containing about 30% to about 50% polyethylene glycol of a molecular weight around 4000. After the fusion, the cells are expanded in suitable culture media as described hereinbefore, supplemented with a selection medium, for example HAT medium, at regular intervals in order to prevent normal myeloma cells from overgrowing the desired hybridoma cells.

In a further embodiment, recombinant DNA comprising an insert coding for a heavy chain variable domain and/or for a light chain variable domain of antibodies directed to the cell line described hereinbefore are produced. The term DNA includes coding single stranded DNAs, double stranded DNAs consisting of said coding DNAs and of complementary DNAs thereto, or these complementary (single stranded) DNAs themselves.

Furthermore, DNA encoding a heavy chain variable domain and/or a light chain variable domain of antibodies directed to the cell line disclosed herein can be enzymatically or chemically synthesized DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. Preferably said modification(s) are outside the CDRs of the heavy chain variable domain and/or of the light chain variable domain of the antibody in humanization and expression optimization applications. The term mutant DNA also embraces silent mutants wherein one or more nucleotides are replaced by other nucleotides with the new codons coding for the same amino acid(s). The term mutant sequence also includes a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Recombinant DNAs including an insert coding for a heavy chain murine variable domain of an antibody directed to the cell line disclosed herein fused to a human constant domain g, for example γ1, γ2, γ3 or γ4, preferably γ1 or γ4 are also provided. Recombinant DNAs including an insert coding for a light chain murine variable domain of an antibody directed to the cell line disclosed herein fused to a human constant domain κ or λ, preferably κ are also provided Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule.

The DNA coding for an effector molecule is intended to be a DNA coding for the effector molecules useful in diagnostic or therapeutic applications. Thus, effector molecules which are toxins or enzymes, especially enzymes capable of catalyzing the activation of prodrugs, are particularly indicated. The DNA encoding such an effector molecule has the sequence of a naturally occurring enzyme or toxin encoding DNA, or a mutant thereof, and can be prepared by methods well known in the art.

Antibodies and antibody fragments disclosed herein are useful in diagnosis and therapy. Accordingly, a composition for therapy or diagnosis comprising an antibody disclosed herein is provided.

In the case of a diagnostic composition, the antibody is preferably provided together with means for detecting the antibody, which may be enzymatic, fluorescent, radioisotopic or other means. The antibody and the detection means may be provided for simultaneous, separate or sequential use, in a diagnostic kit intended for diagnosis.

Uses of the CLL Cell Line

There are many advantages to the development of a CLL cell line, as it provides an important tool for the development of diagnostics and treatments for CLL.

A cell line according to this disclosure may be used for in vitro studies on the etiology, pathogenesis and biology of CLL. This assists in the identification of suitable agents that are useful in the therapy of CLL disease.

The cell line may also be used to produce monoclonal antibodies for in vitro and in vivo diagnosis of CLL, as referred to above, and for the screening and/or characterization of antibodies produced by other methods, such as by panning antibody libraries with primary cells and/or antigens derived from CLL patients.

The cell line may be used as such, or antigens may be derived therefrom. Advantageously, such antigens are cell-surface antigens specific for CLL. They may be isolated directly from cell lines according to this disclosure. Alternatively, a cDNA expression library made from a cell line described herein may be used to express CLL-specific antigens, useful for the selection and characterization of anti-CLL antibodies and the identification of novel CLL-specific antigens.

Treatment of CLL using monoclonal antibody therapy has been proposed in the art. Recently, Hainsworth (Oncologist 5 (5) (2000) 376-384) has described the current therapies derived from monoclonal antibodies. Lymphocytic leukemia in particular is considered to be a good candidate for this therapeutic approach due to the presence of multiple lymphocyte-specific antigens on lymphocyte tumors.

Existing antibody therapies (such as Rituximab™, directed against the CD20-antigen, which is expressed on the surface of B-lymphocytes) have been used successfully against certain lymphocytic disease. However, a lower density CD20 antigen is expressed on the surface of B-lymphocytes in CLL (Almasri et al., Am. J. Hematol., 40 (4) (1992) 259-263).

The CLL cell line described herein thus permits the development of novel anti-CLL antibodies having specificity for one or more antigenic determinants of the present CLL cell line, and their use in the therapy and diagnosis of CLL.

In a particularly useful embodiment, the antibody binds to or otherwise interferes with the metabolic pathway of a polypeptide that is upregulated by a malignant cancer cell. For instance, the antibody can bind to the upregulated polypeptide and in this manner prevent or inhibit the polypeptide from interacting with other molecules or receptors. Alternatively, the antibody may bind to a receptor with which the upregulated polypeptide normally interacts, thereby preventing or inhibiting the polypeptide from binding to the receptor. As yet another alternative, the antibody can bind to an antigen that modulates expression of the polypeptide, thereby preventing or inhibiting normal or increased expression of the polypeptide. For example, the peptide OX-2/CD200 is upregulated in a portion of CLL patients. Because the presence of OX-2/CD200 has been associated with reduced immune response, it would be desirable to interfere with the metabolic pathway of OX-2/CD200 so that the patient's to immune system can defend against the cancer more effectively.

Thus, in another embodiment, a method for treating a cancer patient in accordance with this disclosure includes the steps of screening a cancer patient for the presence of a polypeptide that is upregulated by a malignant cancer cell and administering an antibody that interferes with the metabolic pathway of the upregulated polypeptide. In a particularly useful embodiment, a CLL patient is screened for overexpression of OX-2/CD200 and an antibody that interferes with the metabolic pathway of OX-2/CD200 is administered to the patient. As described in detail below, one such antibody is scFv9 (see FIG. 9B) which binds to OX-2/CD200.

In order that those skilled in the art may be better able to practice the compositions and methods described herein, the following examples are given for illustration purposes.

Example 1

Isolation of Cell Line CLL-AAT

Establishment of the Cell Line

Peripheral blood from a patient diagnosed with CLL was obtained. The WBC count was $1.6 \times 10^8$/ml. Mononuclear cells were isolated by Histopaque-1077 density gradient centrifugation (Sigma Diagnostics, St. Louis, Mo.). Cells were washed twice with Iscove's Modified Dulbecco's Medium (IMDM) supplemented with 10% heat-inactivated fetal bovine serum (FBS), and resuspended in 5 ml of ice-cold IMDM/10% FBS. Viable cells were counted by staining with trypan blue. Cells were mixed with an equal volume of 85% FBS/15% DMSO and frozen in 1 ml aliquots for storage in liquid nitrogen.

Immunophenotyping showed that >90% of the CD45+ lymphocyte population expressed IgD, kappa light chain, CD5, CD19, and CD23. This population also expressed low levels of IgM and CD20. Approximately 50% of the cells expressed high levels of CD38. The cells were negative for lambda light chain, CD10 and CD138

An aliquot of the cells was thawed, washed, and resuspended at a density of $10^7$/mL in IMDM supplemented with 20% heat-inactivated FBS, 2 mM L-glutamine, 100 units/ml penicillin, 100 µg/ml streptomycin, 50 µM 2-mercaptoethanol, and 5 ng/ml recombinant human IL-4 (R & D Systems, Minneapolis, Minn.). The cells were cultured at 37° C. in a humidified 5% CO2 atmosphere. The medium was partially replaced every 4 days until steady growth was observed. After 5 weeks, the number of cells in the culture began to double approximately every 4 days. This cell line was designated CLL-AAT.

Characterization of the Cell Line

Immunophenotyping of the cell line by flow cytometry showed high expression of IgM, kappa light chain, CD23, CD38, and CD138, moderate expression of CD19 and CD20, and weak expression of IgD and CD5. The cell line was negative for lambda light chain, CD4, CD8, and CD10.

Immunophenotyping of the cell line was also done by whole cell ELISA using a panel of rabbit scFv antibodies that had been selected for specific binding to primary B-CLL cells. All of these CLL-specific scFy antibodies also recognized the CLL-AAT cell line. In contrast, the majority of the scFvs did not bind to two cell lines derived from B cell lymphomas: Ramos, a Burkitt's lymphoma cell line, and RL, a non-Hodgkin's lymphoma cell line.

Example 2

Selection of scFv Antibodies for B-CLL-Specific Cell Surface Antigens Using Antibody Phage Display and Cell Surface Panning Immunizations and scFv Antibody Library Construction Peripheral blood mononuclear cells (PBMC) were isolated from blood drawn from CLL patients at the Scripps Clinic (La Jolla, Calif.). Two rabbits were immunized with $2\times10^7$ PBMC pooled from 10 different donors with CLL. Three immunizations, two sub-cutaneous injections followed by one intravenous injection, were done at three week intervals. Serum titers were checked by measuring binding of serum IgG to primary CLL cells using flow cytometry. Five days after the final immunization, spleen, bone marrow, and PBMC were harvested from the animals. Total RNA was isolated from these tissues using Tri-Reagent (Molecular Research Center, Inc). Single-chain Fv (scFv) antibody phage display libraries were constructed as previously described (Barbas et al., (2001) Phage Display: A Laboratory Manual, Cold Spring Harbor Laboratory Press, Cold Spring Harbor, N.Y.). For cell surface panning, phagemid particles from the reamplified library were precipitated with polyethylene glycol (PEG), resuspended in phosphate-buffered saline (PBS) containing 1% bovine serum albumin (BSA), and dialysed overnight against PBS.

Antibody Selection by Cell Surface Panning

The libraries were enriched for CLL cell surface-specific antibodies by positive-negative selection with a magnetically-activated cell sorter (MACS) as described by Siegel et al. (1997, J. Immunol. Methods 206:73-85). Briefly, phagemid particles from the scFv antibody library were pre-incubated in MPBS (2% nonfat dry milk, 0.02% sodium azide in PBS, pH 7.4) for 1 hour at 25° C. to block nonspecific binding sites. Approximately $10^7$ primary CLL cells were labeled with mouse anti-CD5 IgG and mouse anti-CD19 IgG conjugated to paramagnetic microbeads (Miltenyi Biotec, Sunnyvale, Calif.). Unbound microbeads were removed by washing. The labeled CLL cells ("target cells") were mixed with an excess of "antigen-negative absorber cells", pelleted, and resuspended in 50 µl ($10^{10}$-$10^{11}$ cfu) of phage particles. The absorber cells serve to soak up phage that stick non-specifically to cell surfaces as well as phage specific for "common" antigens present on both the target and absorber cells. The absorber cells used were either TF-1 cells (a human erythroleukemia cell line) or normal human B cells isolated from peripheral blood by immunomagnetic negative selection (StemSep system, StemCell Technologies, Vancouver, Canada). The ratio of absorber cells to target cells was approximately 10 fold by volume. After a 30 minute incubation at 25° C., the cell/phage mixture was transferred to a MiniMACS MS+ separation column. The column was washed twice with 0.5 ml of MPBS, and once with 0.5 ml of PBS to remove the unbound phage and absorber cells. The target cells were eluted from the column in 1 ml of PBS and pelleted in a microcentrifuge at maximum speed for 15 seconds. The captured phage particles were eluted by resuspending the target cells in 200 µl of acid elution buffer (0.1 N HCl, pH adjusted to 2.2 with glycine, plus 1 µg/ml BSA). After a 10 minute incubation at 25° C., the buffer was neutralized with 12 µL of 2M Tris base, pH10.5, and the eluted phage were amplified in *E. coli* for the next round of panning. For each round of panning, the input and output phage titers were determined. The input titer is the number of reamplified phage particles added to the target cell/absorber cell mixture and the output titer is the number of captured phage eluted from the target cells. An enrichment factor (E) is calculated using the formula $E=(R_n \text{ output}/R_n \text{ input})/(R_1 \text{ output}/R_1 \text{ input})$. In most cases, an enrichment factor of $10^2$-$10^3$ fold should be attained by the third or fourth round.

Analysis of Enriched Antibody Pools Following Panning

After 3-5 rounds of panning, the pools of captured phage were assayed for binding to CLL cells by flow cytometry and/or whole cell ELISA:

1. To produce an entire pool in the form of HA-tagged soluble antibodies, 2 ml of a non-suppressor strain of *E. coli* (e.g. TOP1OF') was infected with 1 µl ($10^9$-$10^{10}$ cfu) of phagemid particles. The original, unpanned library was used as a negative control. Carbenicillin was added to a final concentration of 10 µM and the culture was incubated at 37° C. with shaking at 250 rpm for 1 hour. Eight ml of SB medium containing 50 µg/ml carbenicillin was added and the culture was grown to an OD 600 of ~0.8. IPTG was added to a final concentration of 1 mM to induce scFv expression from the Lac promoter and shaking at 37° C. was continued for 4 hours. The culture was centrifuged at 3000×g for 15'. The supernatant containing the soluble antibodies was filtered and stored in 1 ml aliquots at −20° C.
2. Binding of the scFv antibody pools to target cells vs. absorber cells was determined by flow cytometry using high-affinity Rat Anti-HA (clone 3F10, Roche Molecular Biochemicals) as secondary antibody and PE-conjugated Donkey Anti-Rat as tertiary antibody.
3. Binding of the antibody pools to target cells vs. absorber cells was also determined by whole-cell ELISA as described below.

Screening Individual scFv Clones Following Panning

To screen individual scFv clones following panning, TOP1OF' cells were infected with phage pools as described above, spread onto LB plates containing carbenicillin and tetracycline, and incubated overnight at 37° C. Individual colonies were inoculated into deep 96-well plates containing 0.6-1.0 ml of SB-carbenicillin medium per well. The cultures were grown for 6-8 hours in a HiGro shaking incubator (Gen-eMachines, San Carlos, Calif.) at 520 rpm and 37° C. At this point, a 90 µl aliquot from each well was transferred to a deep 96-well plate containing 10 µL of DMSO. This replica plate was stored at −80° C. IPTG was added to the original plate to a final concentration of 1 mM and shaking was continued for 3 hours. The plates were centrifuged at 3000×g for 15 minutes. The supernatants containing soluble scFv antibodies were transferred to another deep 96-well plate and stored at −20° C.

A sensitive whole-cell ELISA method for screening HA-tagged scFv antibodies was developed:

1. An ELISA plate is coated with concanavalin A (10 mg/ml in 0.1 M $NaHCO_3$, pH8.6, 0.1 mM $CaCl_2$).
2. After washing the plate with PBS, 0.5-1×$10^5$ target cells or absorber cells in 50 µl of PBS are added to each well, and the plate is centrifuged at 250×g for 10 minutes.
3. 50 µl of 0.02% glutaraldehyde in PBS are added and the cells are fixed overnight at 4° C.
4. After washing with PBS, non-specific binding sites are blocked with PBS containing 4% non-fat dry milk for 3 hours at room temperature.

5. The cells are incubated with 50 μl of soluble, HA-tagged scFv or Fab antibody (TOP1OF' supernatant) for 2 hours at room temperature, then washed six times with PBS.
6. Bound antibodies are detected using a Mouse Anti-HA secondary antibody (clone 12CA5) and an alkaline phosphatase (AP)-conjugated Anti-Mouse IgG tertiary antibody. An about 10-fold amplification of the signal is obtained by using AMDEX AP-conjugated Sheep Anti-Mouse IgG as the tertiary antibody (Amersham Pharmacia Biotech). The AMDEX antibody is conjugated to multiple AP molecules via a dextran backbone. Color is developed with the alkaline phosphatase substrate PNPP and measured at 405 nm using a microplate reader.

Primary screening of the scFv clones was done by ELISA on primary CLL cells versus normal human PBMC. Clones which were positive on CLL cells and negative on normal PBMC were rescreened by ELISA on normal human B cells, human B cell lines, TF-1 cells, and the CLL-AAT cell line. The clones were also rescreened by ELISA on CLL cells isolated from three different patients to eliminate clones that recognized patient-specific or blood type-specific antigens. Results from representative ELISAs are shown in FIGS. 2-6 and summarized in FIGS. 9a-9c.

Figure 9A:
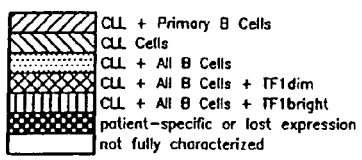

The number of unique scFv antibody clones obtained was determined by DNA fingerprinting and sequencing. The scFv DNA inserts were amplified from the plasmids by PCR and digested with the restriction enzyme BstNI. The resulting fragments were separated on a 4% agarose gel and stained with ethidium bromide. Clones with different restriction fragment patterns must have different amino acid sequences. Clones with identical patterns probably have similar or identical sequences. Clones with unique BstNI fingerprints were further analyzed by DNA sequencing. Twenty-five different sequences were found, which could be clustered into 16 groups of antibodies with closely related complementarity determining regions (FIGS. 9a-9c).

Characterization of scFv Antibodies by Flow Cytometry

The binding specificities of several scFv antibodies were analyzed by 3-color flow cytometry (FIG. 7). PBMC isolated from normal donors were stained with FITC-conjugated anti-CD5 and PerCP-conjugated anti-CD19. Staining with scFv antibody was done using biotin-conjugated anti-HA as secondary antibody and PE-conjugated streptavidin. Three antibodies, scFv-2, scFv-3, and scFv-6, were found to specifically recognize the CD19+ B lymphocyte population (data not shown). The fourth antibody, scFv-9, recognized two distinct cell populations: the CD19+ B lymphocytes and a subset of CD5+ T lymphocytes (FIG. 7). Further characterization of the T cell subset showed that it was a subpopulation of the CD4+CD8" TH cells (data not shown).

Figure 8A:
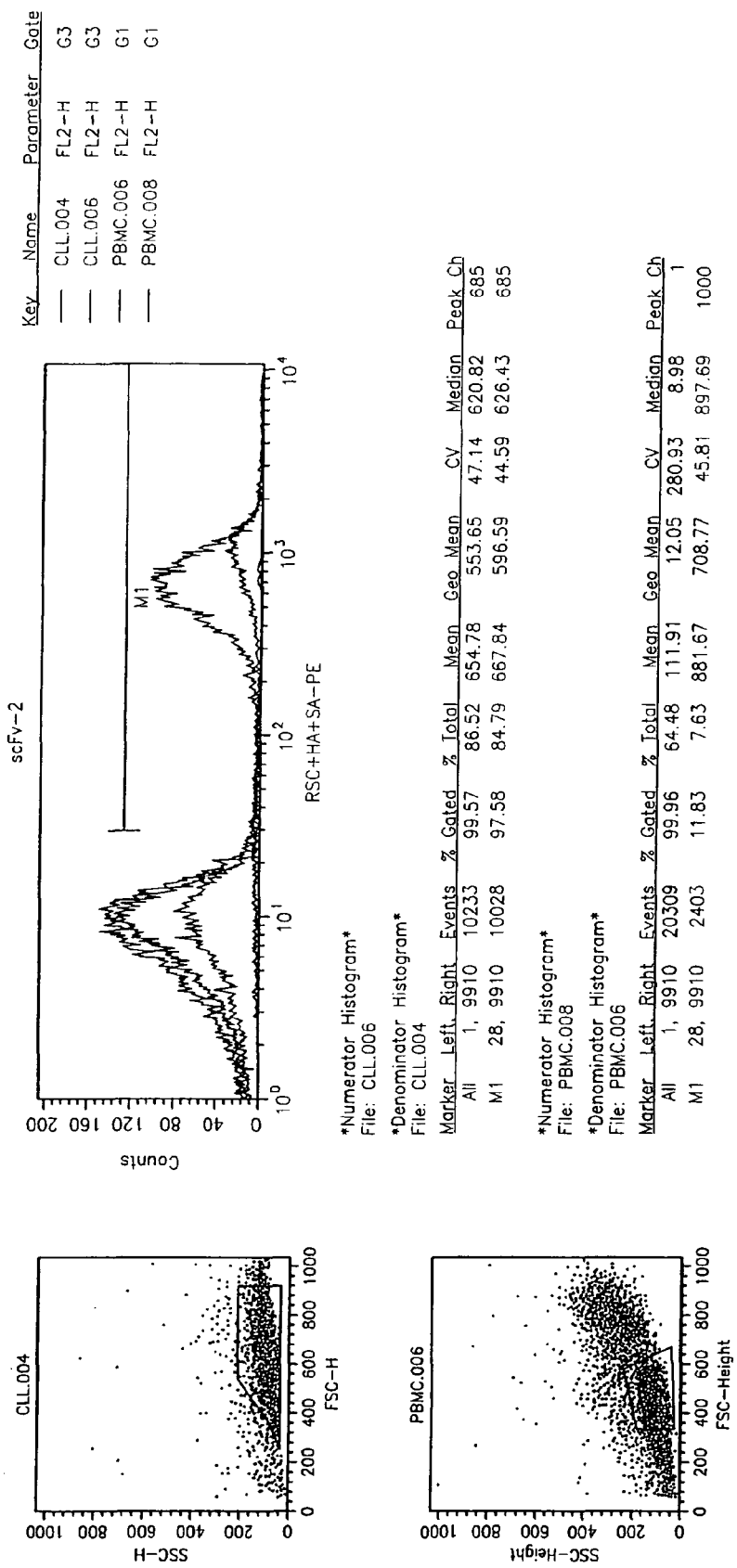
FIGS. 8a, 8b and 8c show the expression levels of antigens recognized by scFv antibodies in accordance with this disclosure. The antigens recognized by scFv-3 and scFv-9 are overexpressed on the primary CLL tumor from which the CLL-AAT cell line was derived. Primary PBMC from the CLL patient used to establish the CLL-AAT cell line or PBMC from a normal donor were stained with scFv antibody and analyzed by flow cytometry. ScFv-3 and scFv-9 stain the CLL cells more brightly than the normal PBMC as measured by the mean fluorescent intensities.
Figure 8B:
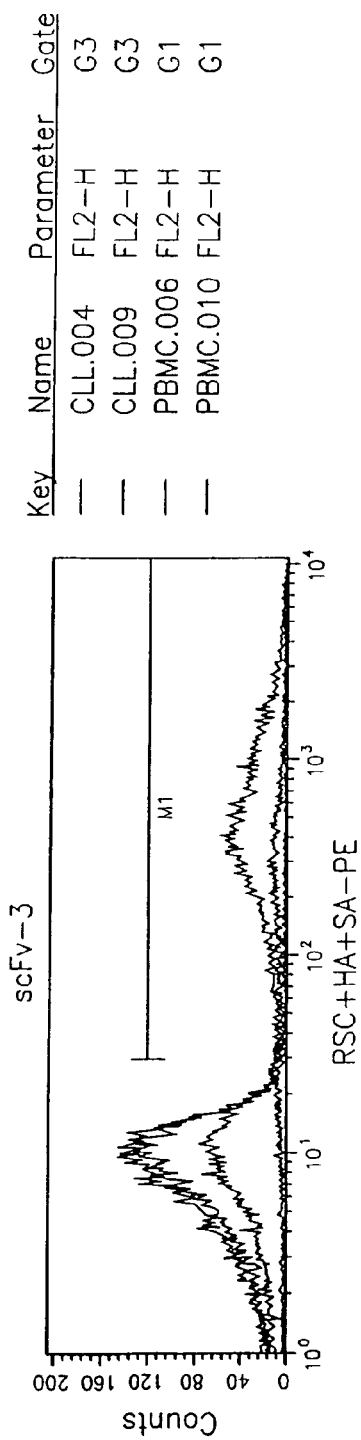
Figure 8C:
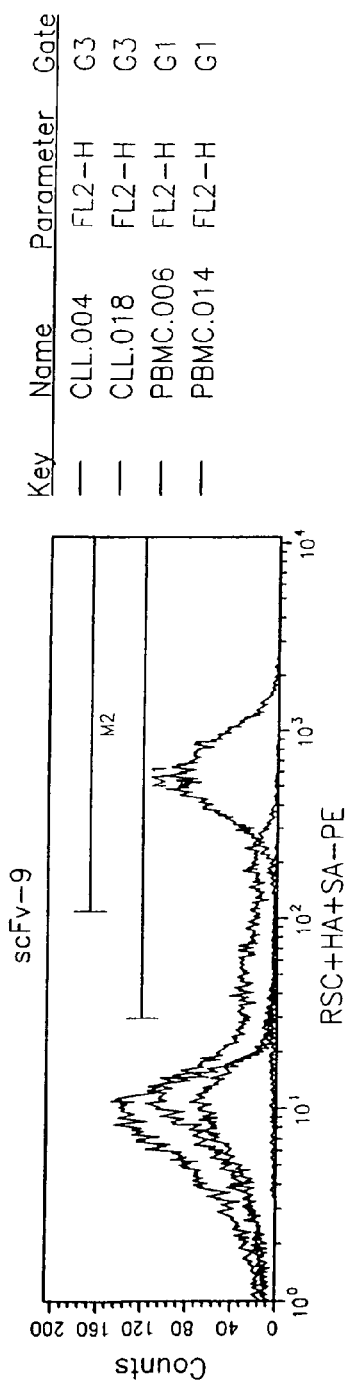

To determine if the antigens recognized by the scFv antibodies were overexpressed on primary CLL cells, PBMC from five CLL patients and five normal donors were stained with scFv and compared by flow cytometry (FIG. 8 and Table 2). By comparing the mean fluorescent intensities of the positive cell populations, the relative expression level of an antigen on CLL cells vs. normal cells could be determined. One antibody, scFv-2, consistently stained CLL cells less intensely than normal PBMC, whereas scFv-3 and scFv-6 both consistently stained CLL cells more brightly than normal PBMC. The fourth antibody, scFv-9, stained two of the five CLL samples much more intensely than normal PBMC, but gave only moderately brighter staining for the other three CLL samples (FIG. 8 and Table 2). This indicates that the antigens for scFv-3 and scFv-6 are overexpressed approximately 2-fold on most if not all CLL tumors, whereas scFv-9 is overexpressed 3 to 6-fold on a subset of CLL tumors.

CLL patients can be divided into two roughly equal groups: those with a poor prognosis (median survival time of 8 years) and those with a favorable prognosis (median survival time of 26 years). Several unfavorable prognostic indicators have been identified for CLL, most notably the presence of VH genes lacking somatic mutations and the presence of a high percentage of $CD38^+$ B cells. Since scFv-9 recognizes an antigen overexpressed in only a subset of CLL patients, we sought to determine if scFv-9 antigen overexpression correlated with the percentage of $CD38^+$ cells in blood samples from ten CLL patients (FIG. 11). The results indicate that scFv-9 antigen overexpression and percent $CD38^+$ cells are completely independent of one another.

Identification of Antigens Recognized by scFv Antibodies by Immunoprecipitation (IP) and Mass Spectrometry (MS)

Figure 12:
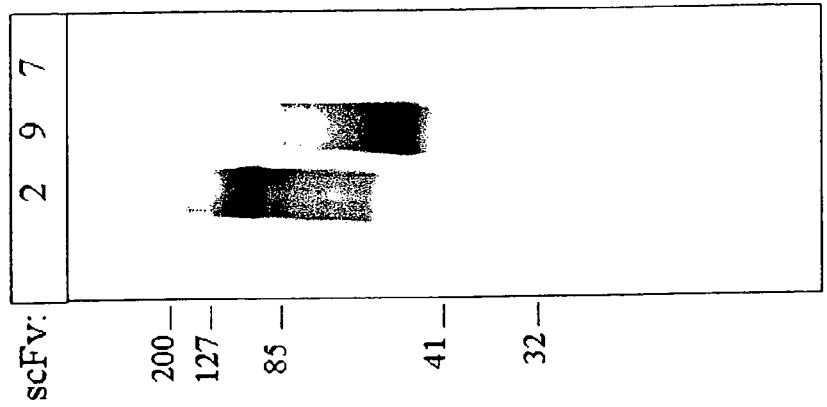
FIG. 12. shows the identification of scFv antigens by immunoprecipitation and mass spectrometry. CLL-AAT cells were labeled with a solution of 0.5 mg/ml sulfo-NHS-LC-biotin (Pierce) in PBS, pH8.0 for 30'. After extensive washing with PBS to remove unreacted biotin, the cells were disrupted by nitrogen cavitation and the microsomal fraction was isolated by differential centrifugation. The microsomal fraction was resuspended in NP40 Lysis Buffer and extensively precleared with normal rabbit serum and protein A sepharose. Antigens were immunoprecipitated with HA-tagged scFv antibodies coupled to Rat Anti-HA agarose beads (Roche). Following immunoprecipitation, antigens were separated by SDS-PAGE and detected by Western blot using streptavidin-alkaline phosphatase (AP) or by Coomassie G-250 staining. ScFv-7, an antibody which doesn't bind to CLL-AAT cells, was used as a negative control. Antigen bands were excised from the Coomassie-stained gel and identified by mass spectrometry (MS). MALDI-MS was performed at the Proteomics Core Facility of The Scripps Research Institute (La Jolla, Calif.). μLC/MS/MS was performed at the Harvard Microchemistry Facility (Cambridge, Mass.).
Figure 13:
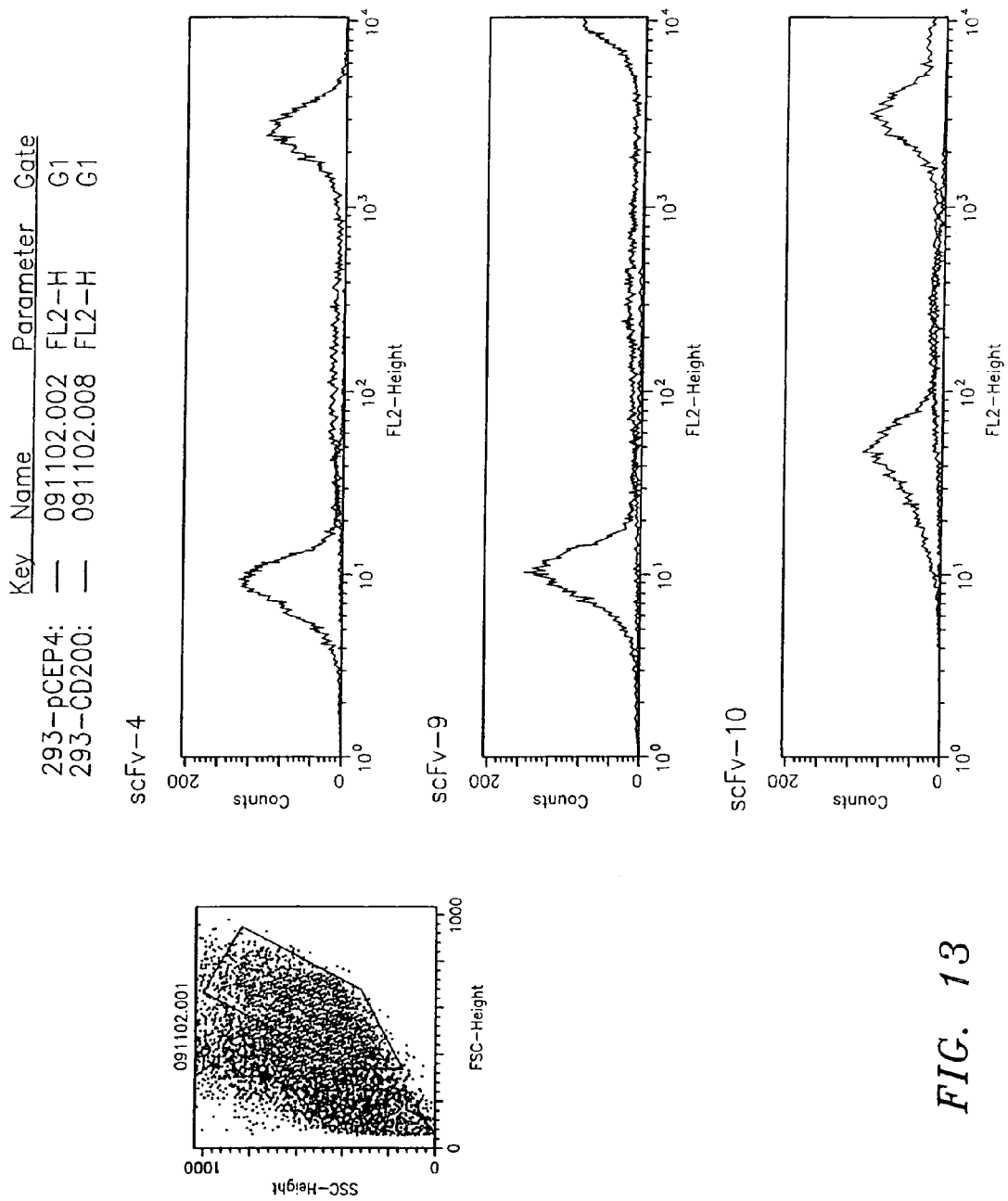
FIG. 13. shows that three scFv antibodies bind specifically to 293-EBNA cells transiently transfected with a human OX-2/CD200 cDNA clone. A CD200 cDNA was cloned from CLL cells by RT-PCR and inserted into the mammalian expression vector pCEP4 (Invitrogen). PCEP4-CD200 plasmid or the corresponding empty vector pCEP4 was transfected into 293-EBNA cells using Polyfect reagent (QIAGEN). Two days after transfection, the cells were analyzed for binding to scFv antibodies by flow cytometry.

To identify the antigens for these antibodies, scFvs were used to immunoprecipitate the antigens from lysates prepared from the microsomal fraction of cell-surface biotinylated CLL-AAT cells (FIG. 12). The immunoprecipitated antigens were purified by SDS-PAGE and identified by matrix assisted laser desorption ionization mass spectrometry (MALDI-MS) or microcapillary reverse-phase HPLC nano-electrospray tandem mass spectrometry (μLC/MS/MS) (data not shown). ScFv-2 immunoprecipitated a 110 kd antigen from both RL and CLL-AAT cells (FIG. 12). This antigen was identified by MALDI-MS as the B cell-specific marker CD19. ScFv-3 and scFv-6 both immunoprecipitated a 45 kd antigen from CLL-AAT cells (not shown). This antigen was identified by MALDI-MS as CD23, which is a known marker for CLL and activated B cells. ScFv-9 immunoprecipitated a 50 kd antigen from CLL-AAT cells (FIG. 12). This antigen was identified by μLC/MS/MS as OX-2/CD200, a known marker for B cells, activated $CD4^+$ T cells, and thymocytes. OX-2/CD200 is also expressed on some non-lymphoid cells such as neurons and endothelial cells.

REFERENCES

The following references are incorporated herein by reference to more fully describe the state of the art to which the present invention pertains. Any inconsistency between these publications below or those incorporated by reference above and the present disclosure shall be resolved in favor of the present disclosure.

Almasri, N M et al. (1992). Am J Hemato 140 259-263.
10 Hainsworth, J D (2000). Oncologist 2000; 5(5):376-84
Nilsson, K (1992). Bum Cell. 5(1):25-41.
Pu, Q Q and Bezwoda, W (2000). Anticancer Res. 20(4): 2569-78.
Walls A V et al. (1989). Int. J. Cancer 44846-853.

It will be understood that various modifications may be made to the embodiments disclosed herein. For example, as those skilled in the art will appreciate, the specific sequences described herein can be altered slightly without necessarily adversely affecting the functionality of the antibody or antibody fragment. For instance, substitutions of single or multiple amino acids in the antibody sequence can frequently be made without destroying the functionality of the antibody or fragment. Thus, it should be understood that antibodies having a degree of homology greater than 70% to the specific antibodies described herein are within the scope of this disclosure. In particularly useful embodiments, antibodies having a homology greater than about 80% to the specific antibodies described herein are contemplated. In other useful embodiments, antibodies having a homology greater than about 90% to the specific antibodies described herein are contemplated. Therefore, the above description should not be construed as limiting, but merely as exemplifications of preferred embodiments. Those skilled in the art will envision other modifications within the scope and spirit of this disclosure.

The invention claimed is:

1. The cell line CLL-AAT deposited under ATCC Accession No. PTA-3920.

\* \* \* \* \*